| (12) | United States Patent<br>Mather et al. | (10) Patent No.: US 10,524,831 B2<br>(45) Date of Patent: Jan. 7, 2020 |
|---|---|---|

(54) MIS ACCESS PORT AND METHODS OF USING

(71) Applicant: SpineCraft, LLC, Westmont, IL (US)

(72) Inventors: Steven E. Mather, Hillsdale, IL (US); Wagdy W. Asaad, Burr Ridge, IL (US)

(73) Assignee: SpineCraft, LLC, Westmont, IL (US)

( * ) Notice: Subject to any disclaimer, the term of this patent is extended or adjusted under 35 U.S.C. 154(b) by 308 days.

(21) Appl. No.: 15/066,734

(22) Filed: Mar. 10, 2016

(65) Prior Publication Data

US 2016/0270816 A1    Sep. 22, 2016

Related U.S. Application Data

(60) Provisional application No. 62/136,424, filed on Mar. 20, 2015.

(51) Int. Cl.
| *A61B 17/34* | (2006.01) |
|---|---|
| *A61B 1/07* | (2006.01) |
| *A61B 1/00* | (2006.01) |
| *A61B 90/30* | (2016.01) |
| *A61B 17/02* | (2006.01) |
| *A61B 50/20* | (2016.01) |
| *A61B 17/00* | (2006.01) |
| *A61F 2/46* | (2006.01) |

(52) U.S. Cl.
CPC ...... *A61B 17/3423* (2013.01); *A61B 1/00128* (2013.01); *A61B 1/00131* (2013.01); *A61B 1/07* (2013.01); *A61B 90/30* (2016.02); *A61B 17/3421* (2013.01); *A61B 50/20* (2016.02); *A61B 2017/00477* (2013.01); *A61B 2017/0256* (2013.01); *A61B 2090/306* (2016.02); *A61F 2/46* (2013.01)

(58) Field of Classification Search
CPC .................................................. A61B 17/3423
See application file for complete search history.

(56) References Cited

U.S. PATENT DOCUMENTS

| 4,181,123 | A | * | 1/1980 | Crosby | ................... | A61B 1/07 |
|---|---|---|---|---|---|---|
| | | | | | | 600/184 |
| 5,785,648 | A | * | 7/1998 | Min | ........................ | A61B 1/32 |
| | | | | | | 600/206 |
| 6,616,603 | B1 | * | 9/2003 | Fontana | ................... | A61B 1/31 |
| | | | | | | 600/170 |
| 7,594,888 | B2 | | 9/2009 | Raymond et al. | | |
| 7,874,982 | B2 | | 1/2011 | Selover et al. | | |
| 7,887,548 | B2 | | 2/2011 | Usher, Jr. et al. | | |
| 8,216,185 | B2 | | 7/2012 | Berger | | |
| 2004/0143169 | A1 | * | 7/2004 | Branch | ................. | A61B 90/36 |
| | | | | | | 600/245 |
| 2005/0277811 | A1 | * | 12/2005 | Richards | ................ | A61B 1/303 |
| | | | | | | 600/184 |
| 2008/0319432 | A1 | | 12/2008 | Ely et al. | | |

(Continued)

*Primary Examiner* — Olivia C Chang
(74) *Attorney, Agent, or Firm* — Law Office of Alan W. Cannon

(57) ABSTRACT

An access port for minimally invasive surgery includes an elongate, tubular main body portion, a connector configured to fix at least a portion of the access port to a stationary object; and a slot extending over a length of the main body portion in a lengthwise direction, wherein the slot extends through a wall of the main body portion, from an outside surface of the main body portion to an inside surface of the main body portion.

32 Claims, 28 Drawing Sheets

(56) References Cited

U.S. PATENT DOCUMENTS

2011/0022165 A1* 1/2011 Oba ................... A61B 17/3423
623/2.11
2014/0243604 A1 8/2014 Vennard et al.

* cited by examiner

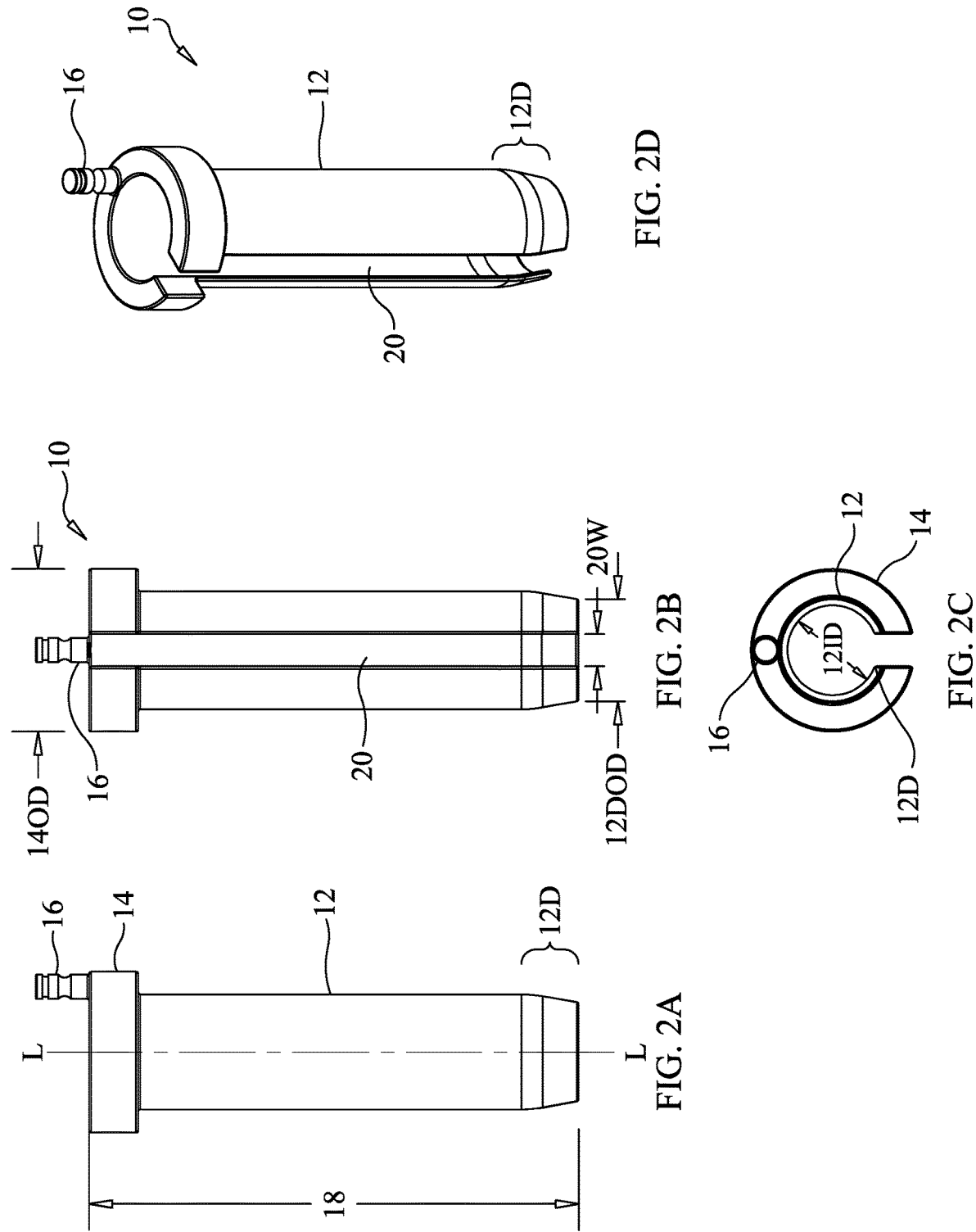

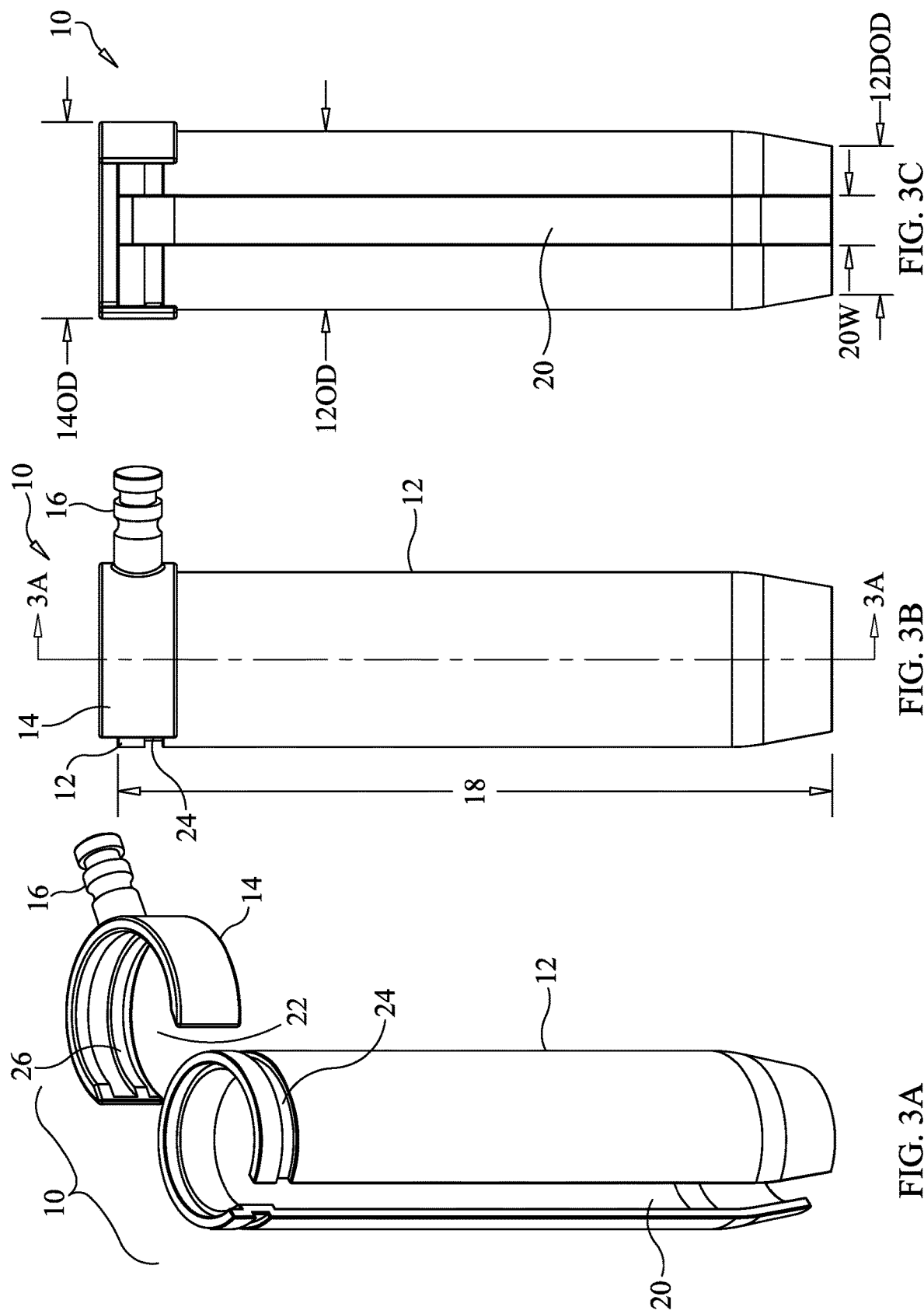

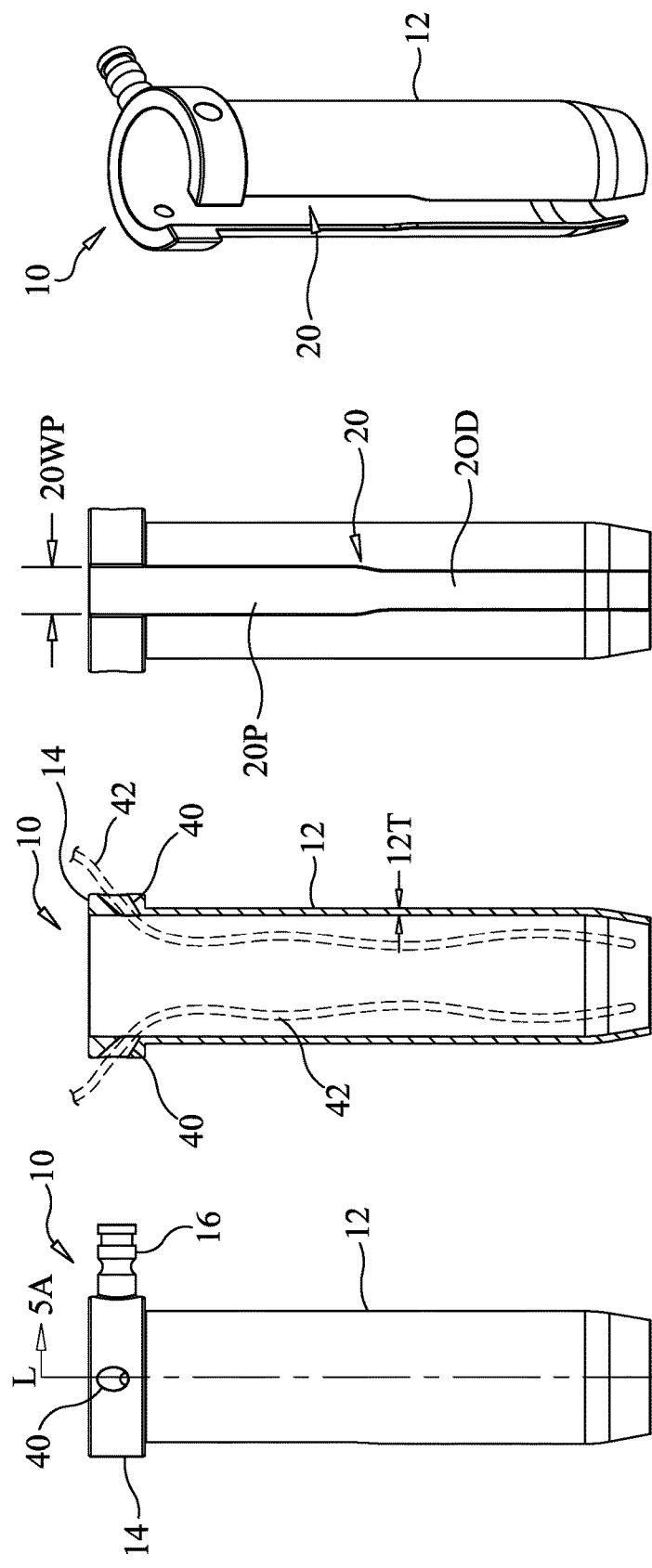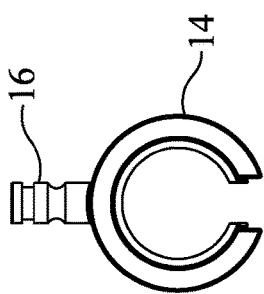
FIG. 5E
FIG. 5C
FIG. 5D
FIG. 5B
FIG. 5A

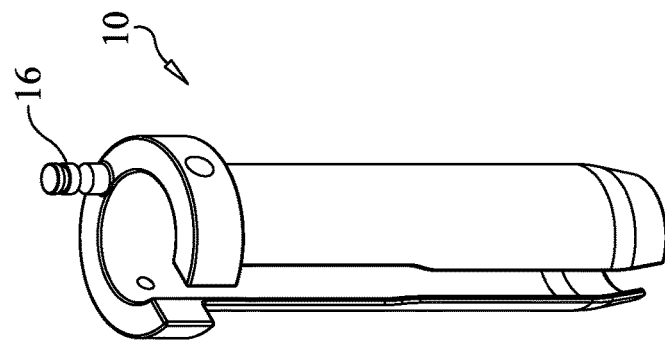
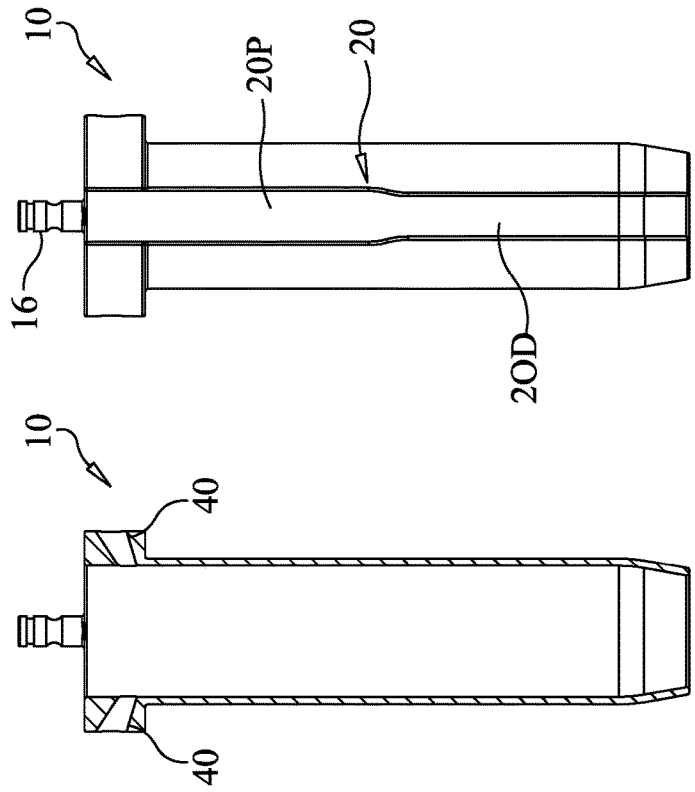
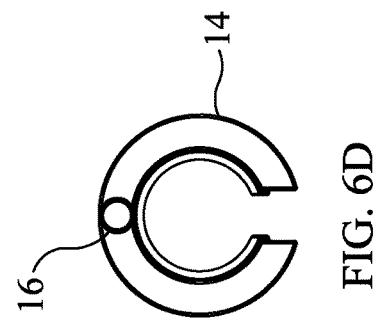
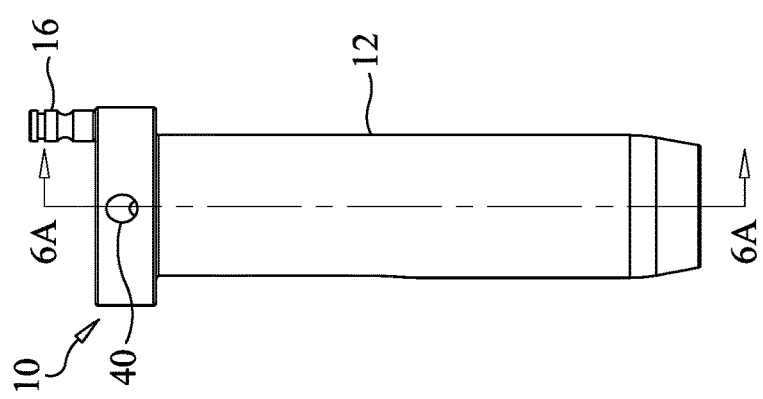
FIG. 6E
FIG. 6C
FIG. 6D
FIG. 6B
FIG. 6A

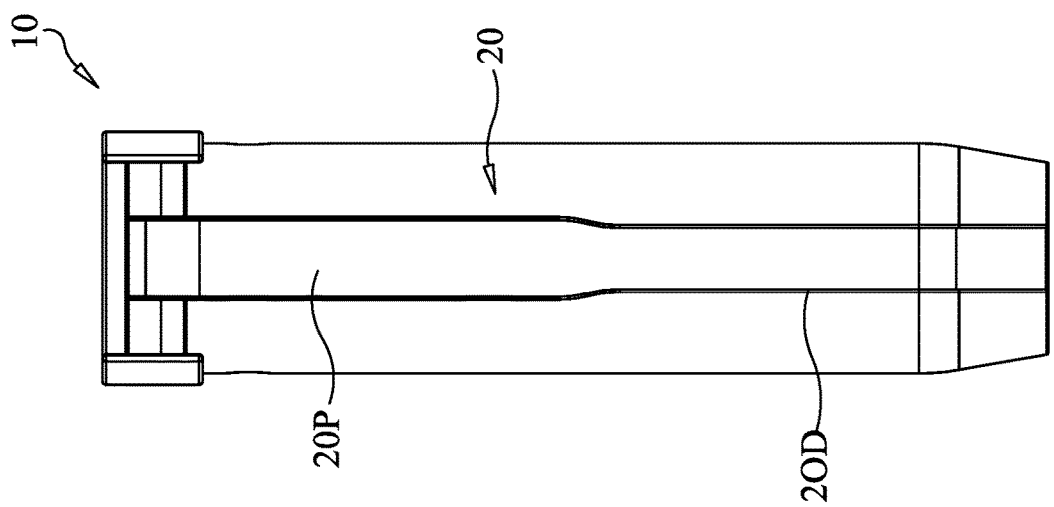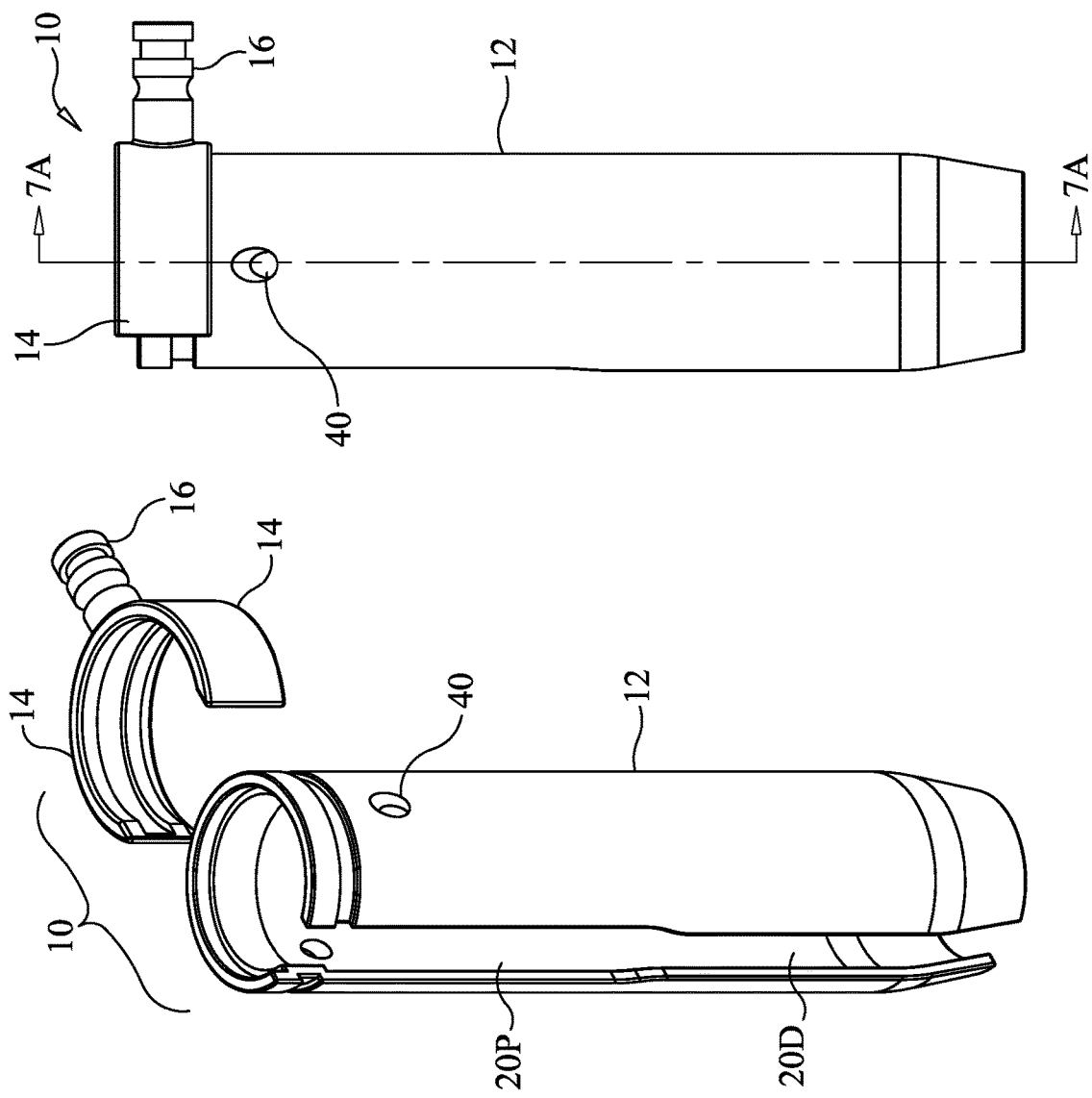

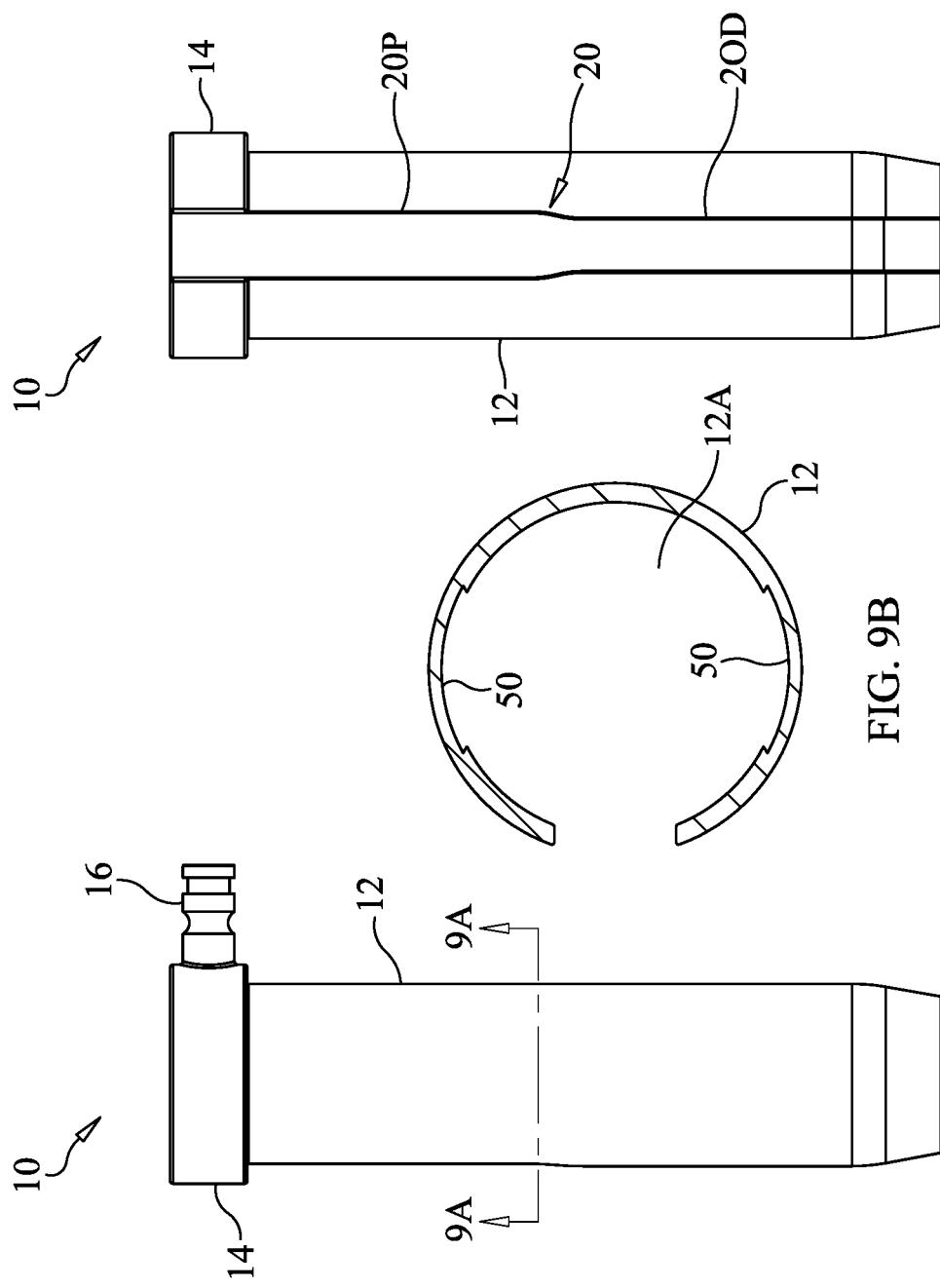

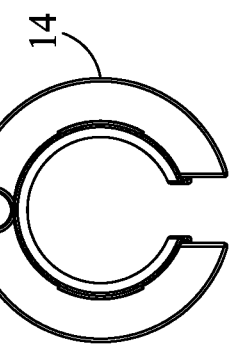
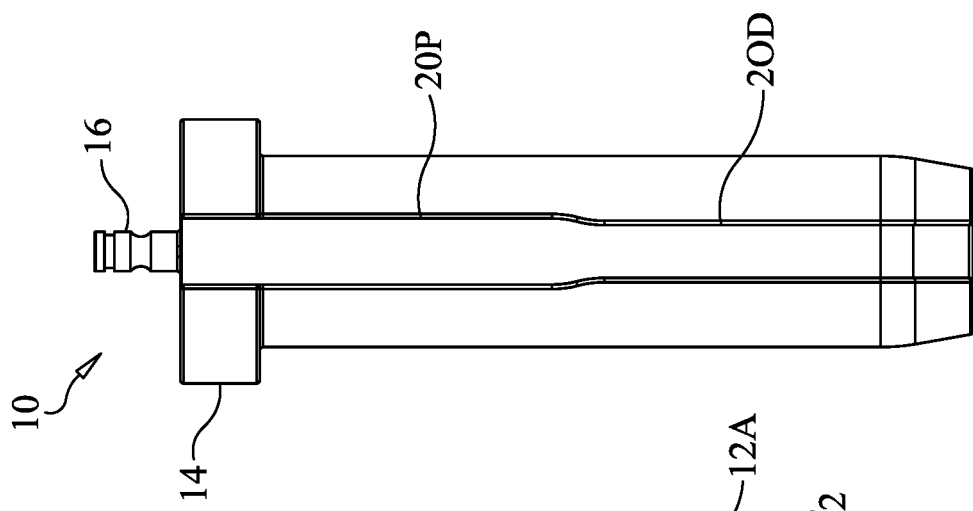
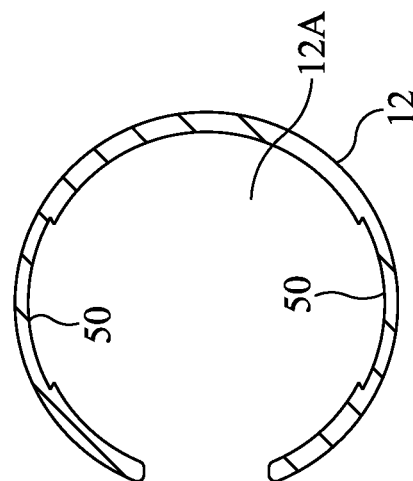
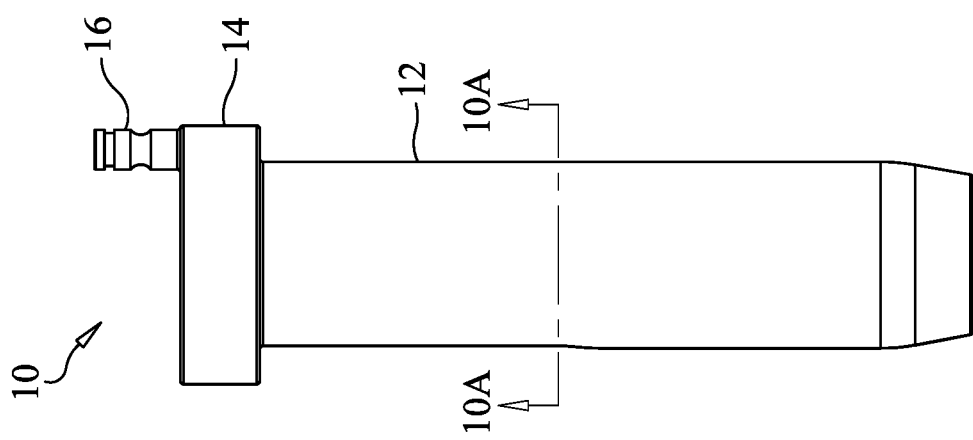
FIG. 10D
FIG. 10C
FIG. 10B
FIG. 10A

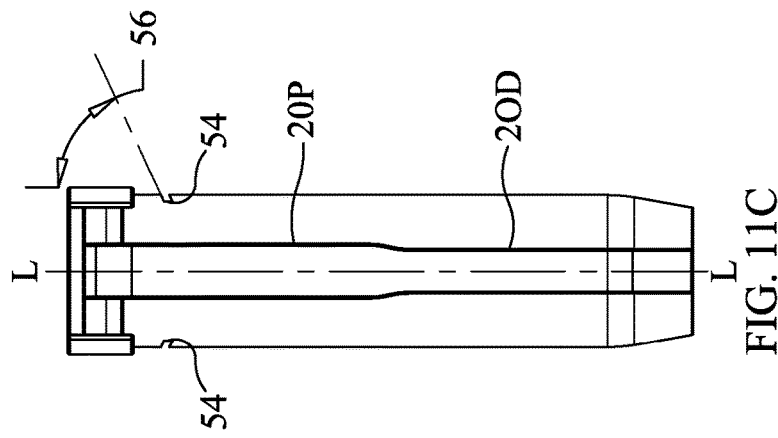
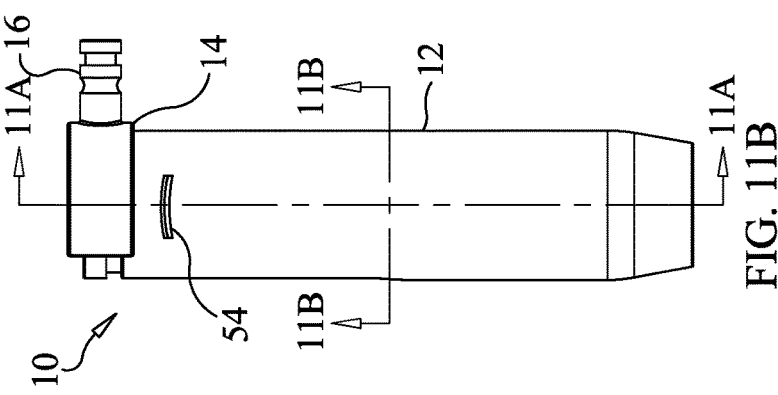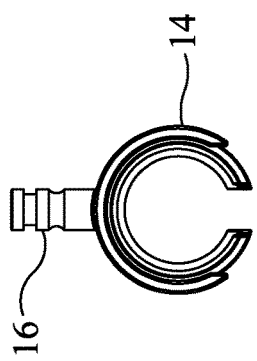
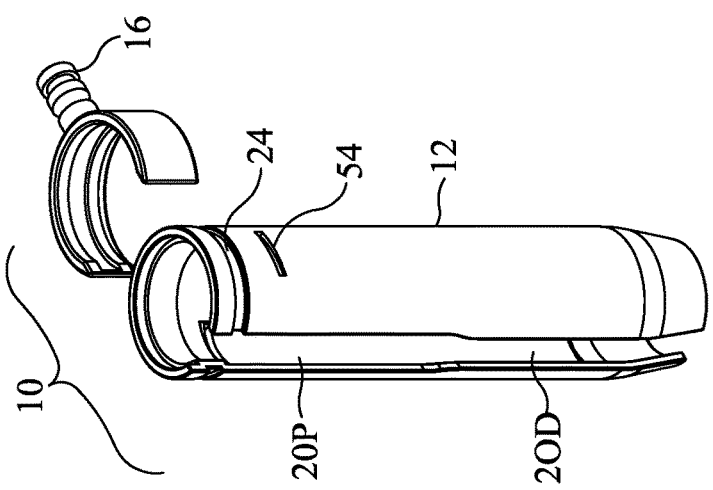

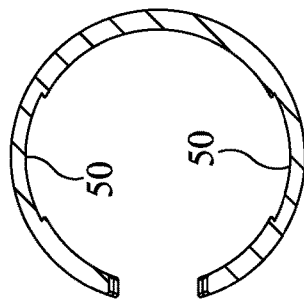
FIG. 12G
FIG. 12I
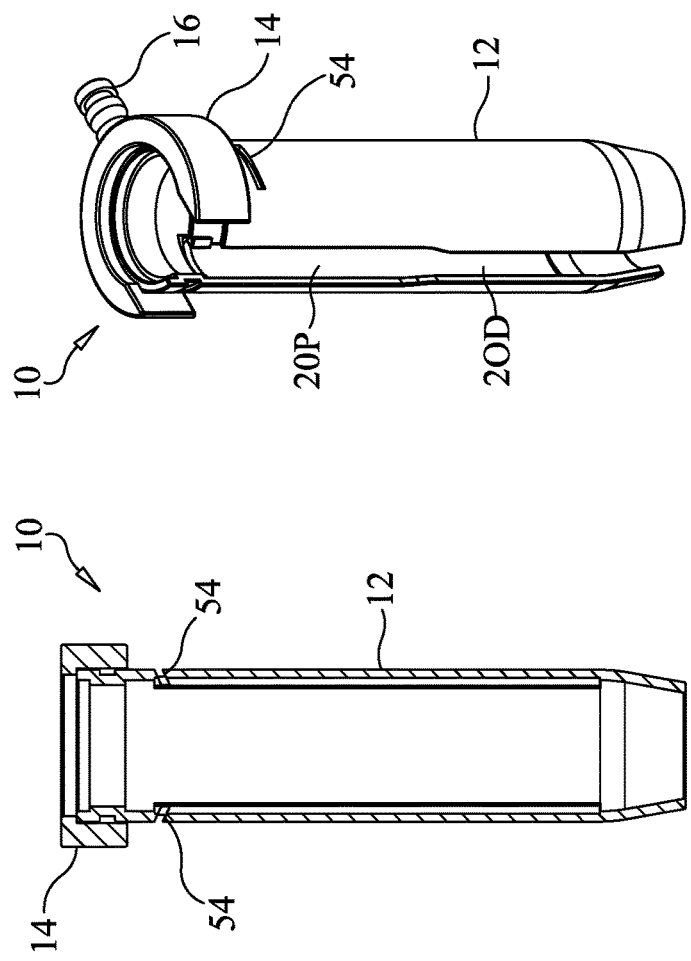
FIG. 12F
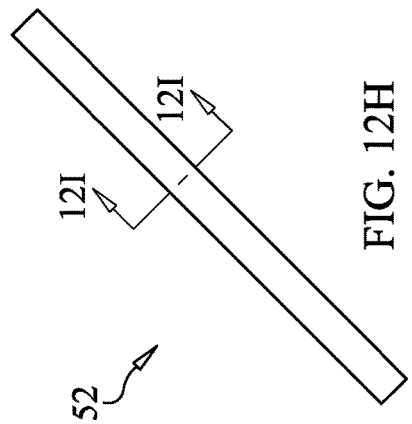
FIG. 12H
FIG. 12E

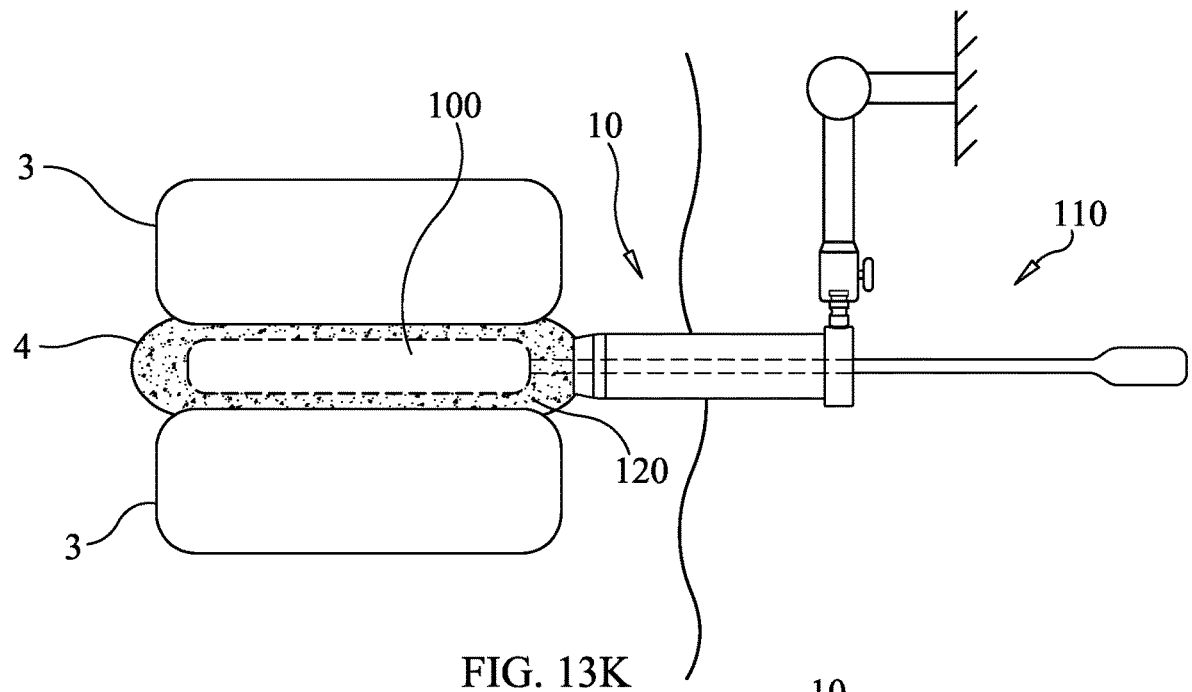
FIG. 13K
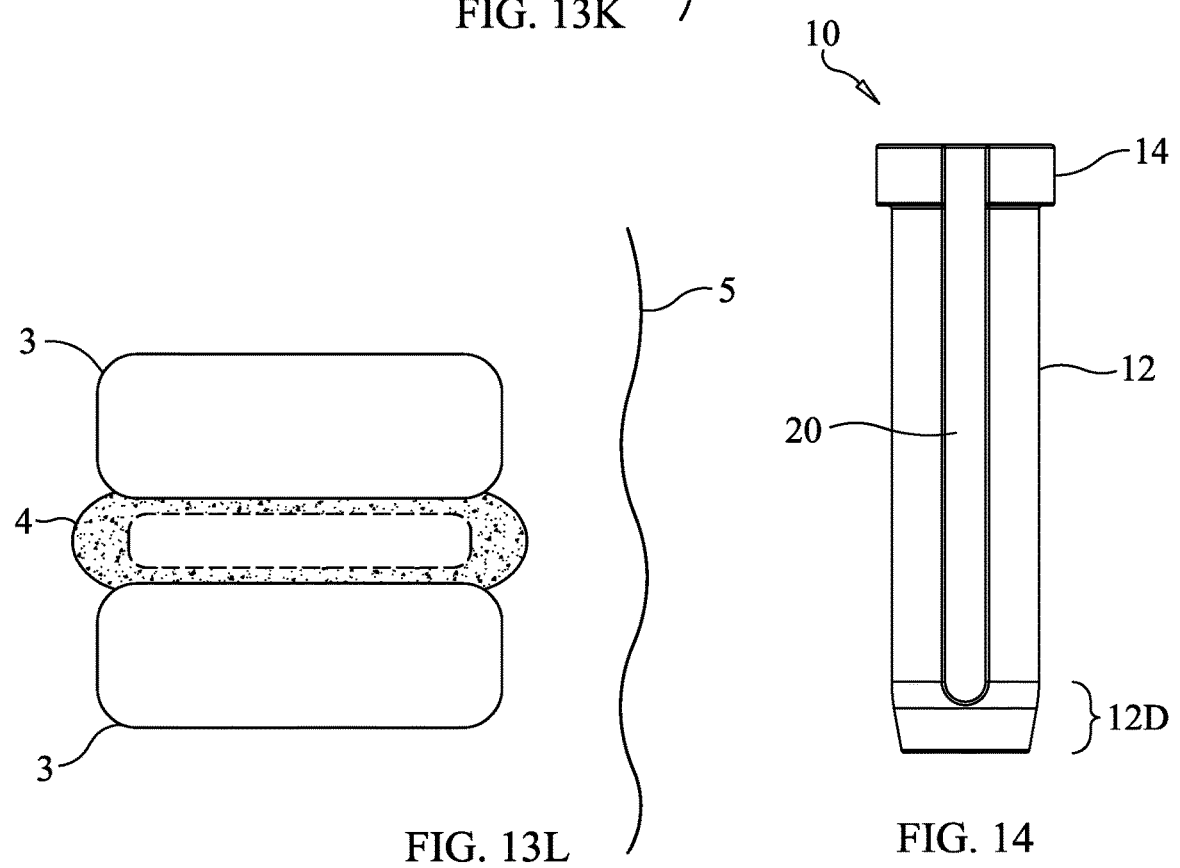
FIG. 13L
FIG. 14

MIS ACCESS PORT AND METHODS OF USING

FIELD OF THE INVENTION

The present invention relates to minimally-invasive surgery. More particularly the prevent invention relates to minimally-invasive spinal surgery.

BACKGROUND OF THE INVENTION

Spinal fusion procedures may involve the remove of a herniated disk and cleaning all of the debris out of the disk space prior to introducing an implant such as a cage or the like and grafting material. To perform such procedures as minimally-invasive surgery (MIS), it can be difficult, if not impossible to remove all of the fragments of the disk or any other debris that might impede the proper insertion and placement of one or more implants and, optionally grafting material. One of the major causes of this difficulty is that access ports or other tubes used to allow the surgeon to access the surgical site place significant restrictions on the mobility of the instruments being used by the surgeon to remove the disk, disk fragments and debris.

U.S. Patent Application Publication No. 2014/0243604 provides a surgical access tube that is provided with oppositely positioned weakened distal portions that can be removed to afford lateral intrusions of the spinous process and facet, respectively, to allow placement of the access tube over the spinous process and facet during a surgical procedure. The break-away, weakened distal portions simplify the fitting of the access tube, making it easier to use than previous tubes that the surgeons had previously used after selectively resecting some portion of the distal end of the tube not having the weakened sections. A weakened proximal portion may also be provided to improve a range of angles for surgical instruments working through the access tube. The weakened proximal section is limited to a height of about 15-20 mm and weakened sections converge from a wider base opening (either at the distal end or proximal end of the access tube) to an arc base, presumably to avoid crack propagation and maintain rigidity of the access tube. Due to the limited height and sweep angle defined by the weakened proximal section, angulation of instruments is limited to only about 25 degrees, possibly up to 30 degrees. Further, the tube must be installed in a predetermined orientation relative to the spinous process and facet and therefore does not allow the tube to be rotated about its longitudinal axis, thereby further limiting the ability to angulate instruments inserted therethrough. It would be desirable to provide solutions that would allow a greater range of angulation of instruments used in an access tube.

U.S. Pat. No. 7,594,888 discloses expandable ports that can be used in minimally invasive surgery. The expandable ports are typically enclosed along the lengths thereof, even after expansion, but some embodiments, such as in FIGS. 17, 18, 29 and 23 result in proximal and distal gaps at the location of expansion. Such gaps are merely the result of the mechanism used to expand the tube. Further, these embodiments retain an impediment such as a mechanism intermediate the proximal and distal gaps which would limit angulation much in the same way described above that angulation is limited in U.S. Patent Application Publication No. 2014/0243604.

There is a need for improved products and methods that allow greater mobility of surgical instruments during MIS surgery, particularly MIS spine surgery.

There is a need for improved products and methods that provide greater, more consistent visibility during MIS surgery, eliminating or significantly reducing shadows and "dead spots" in the visibility field.

SUMMARY OF THE INVENTION

According to one aspect of the present invention, an access port is configured and dimensioned for use in minimally invasive surgery. The access port includes: an elongate, tubular main body portion; a connector configured to fix at least a portion of the access port to a stationary object; and a slot extending over a length of said main body portion in a lengthwise direction, wherein the slot has a length and a width and extends through a wall of the main body portion, from an outside surface of the main body portion to an inside surface of the main body portion; and wherein the width of the slot is substantially constant over at least a third of the length of the slot.

In at least one embodiment, the slot extends a full length of the main body portion, from a proximal end to a distal end of the main body portion.

In at least one embodiment, the width of the slot is substantially constant over the entire length of the slot.

In at least one embodiment, the slot allows an instrument inserted into the main body portion to be angled relative to a longitudinal axis of the main body portion by an angle greater than thirty degrees.

In at least one embodiment, the access port further includes a ring portion at a proximal end of the access port, wherein the connector is rigidly fixed to the ring portion.

In at least one embodiment, the ring portion is integral with the main body portion.

In at least one embodiment, the main body portion has a first outside diameter and the ring portion has a second outside diameter, and wherein the second outside diameter is greater than the first outside diameter.

In at least one embodiment, the slot extends through the ring portion.

In at least one embodiment, the main body portion is rotatable relative to the ring portion, about a longitudinal axis of the main body portion.

In at least one embodiment, the slot is a first slot, and wherein the ring portion comprises a second slot that aligns with the first slot when the ring portion is mounted on the main body portion.

In at least one embodiment, the first slot has a first width and the second slot has a second width, wherein the second width is greater than the first width to allow the second slot to remain aligned with the first slot upon rotation of the main body portion relative to the ring portion.

In at least one embodiment, the slot is tapered such that the slot has a first width along a proximal portion thereof and a second width along a distal portion thereof, wherein the first width is greater than the second width.

In at least one embodiment, the connector is substantially aligned with a longitudinal axis of the main body portion.

In at least one embodiment, the connector is substantially perpendicular to a longitudinal axis of the main body portion.

In at least one embodiment, a distal end portion of the main body portion is tapered.

In at least one embodiment, the main body portion comprises a groove extending circumferentially in an outer surface of a proximal end portion of the main body portion; wherein the ring portion comprises a ledge extending radially inward from an inner surface of the ring portion; and wherein the ledge mates with the groove upon mounting the ring portion to the main body portion.

In at least one embodiment, the main body portion comprises a groove extending circumferentially in an outer surface of a proximal end portion of the main body portion and at least one cutout in the outer surface extending to a proximal end of the main body and communicating with the groove; wherein the ring portion comprises at least one tab extending radially inward from an inner surface of the ring portion, the at least one tab being configured and dimensioned to slide through the at least one cutout, respectively; wherein, upon mounting the ring portion to the main body portion, the at least one tab passes through the at least one cutout and into the groove; and wherein upon rotating the ring portion relative to the main body portion, the at least one tab is prevented from passing back out of the at least one cutout.

In at least one embodiment, the access port further includes at least one lighting implement extending to at least an inner wall surface of the main body portion in an annulus of the main body portion.

In at least one embodiment, the access port further includes at least one light port extending from an outside surface of the access port to an inside surface of the access port; and at least one lighting implement extending into the at least one light port to illuminate at least a portion of the main body portion in an annulus of the main body portion.

In at least one embodiment, the at least one light port extends through the ring portion.

In at least one embodiment, the access port further includes at least one longitudinally extending cutout in an inner wall of the main body portion; and at least one light strip mounted in the at least one longitudinally extending cutout, respectively.

In at least one embodiment, the at least one light strip is flush with the inner wall of the main body portion.

In at least one embodiment, the access port further includes at least one slot extending through a wall of the main body portion and communicating with the at least one cutout, respectively, wherein the at least one slot is configured and dimensioned to allow the at least one light strip to be inserted therethrough and installed in the at least one cutout, respectively.

In at least one embodiment, the access port is provided in combination with an instrument extending through the access port, wherein a distal end of the instrument extends distally of a distal end of the access port and a shaft of the instrument extends through the slot, to provide increased range of motion of the distal end of the instrument.

In at least one embodiment, the access port is configured and dimensioned for use in minimally invasive spine surgery.

In at least one embodiment, the access port includes a light guide assembly installed in a proximal end portion of the tubular main body portion, wherein the light guide assembly includes a fiber optic cable having optical fibers. The optical fibers are fanned out over an inner circumference of the proximal end portion of the tubular opening of the main body to provide even lighting throughout the tubular opening and a surgical target targeted by a distal end opening of the tubular opening.

In at least one embodiment, the light guide assembly further includes a split compression ring. The optical fibers are adhered or otherwise attached to the split compression ring and terminate at or proximal of a distal end of the split compression ring.

According to another aspect of the present invention, a light guide assembly is provided that includes a fiber optic cable having optical fibers, and a split compression ring. The optical fibers are fanned out over an outer circumference of the split compression ring and attached thereto. The optical fibers terminate at or proximal of a distal end of the split compression ring.

In at least one embodiment, the split compression ring is configured and dimensioned to form a compression fit with a tubular opening of an access port.

According to another aspect of the present invention, a method of performing minimally invasive surgery includes: inserting an access port through the skin of a patient and positioning the access port adjacent or into a surgical target location, wherein the access port includes an elongate, tubular main body portion and a slot extending over a length of the main body portion in a lengthwise direction, wherein the slot extends through a wall of the main body portion, from an outside surface of the main body portion to an inside surface of the main body portion; inserting an instrument through the access port such that a distal end portion of the instrument extends into the surgical target location; and manipulating the instrument to pass a shaft portion of the instrument through at least a portion of the slot.

In at least one embodiment, the method further includes fixing at least a portion of the access port to a stationary object.

In at least one embodiment, the access port includes a ring portion at a proximal end portion thereof, the ring portion including a connector extending therefrom, wherein the ring portion is fixed to the stationary object by the connector.

In at least one embodiment, the main body portion is rotatable relative to the ring portion, the method further comprising rotating the main body portion relative to the ring portion to further increase the range of motion of the instrument.

In at least one embodiment, the surgical target location is in the spine of the patient.

In at least one embodiment, the surgical target location is an intervertebral disk space.

These and other advantages and features of the invention will become apparent to those persons skilled in the art upon reading the details of the devices and methods as more fully described below.

BRIEF DESCRIPTION OF THE DRAWINGS

FIG. 2A is a plan view of an access port according to another embodiment of the present invention.

FIG. 2B is a plan view of the access port of FIG. 2A after rotating it about its longitudinal axis by ninety degrees.

FIG. 2C is a top view of the access port of FIG. 2B.

FIG. 2D is a perspective view of the access port of FIGS. 2A-2C.

FIG. 3A is a plan view of a disassembled access port according to another embodiment of the present invention.

FIG. 3B is a plan view of the access port of FIG. 3B after assembly

FIG. 3C is a plan view of the access port of FIG. 3B after rotating it about its longitudinal axis by ninety degrees.

FIG. 5A is a plan view of an access port according to another embodiment of the present invention.

FIG. 5B is a longitudinal section view of the access port of FIG. 5A taken along line 5A-5A.

FIG. 5C is a plan view of the access port of FIG. 5A after rotating it about its longitudinal axis by ninety degrees.

FIG. 5D is a top view of the access port of FIG. 5C.

FIG. 5E is a perspective view of the access port of FIGS. 5A-5D.

FIG. 6A is a plan view of an access port according to another embodiment of the present invention.

FIG. 6B is a longitudinal section view of the access port of FIG. 6A taken along line 6A-6A.

FIG. 6C is a plan view of the access port of FIG. 6A after rotating it about its longitudinal axis by ninety degrees.

FIG. 6D is a top view of the access port of FIG. 6C.

FIG. 6E is a perspective view of the access port of FIGS. 6A-6D.

FIG. 7A is a plan view of a disassembled access port according to another embodiment of the present invention.

FIG. 7B is a plan view of the access port of FIG. 7A after assembly.

FIG. 7C is a plan view of the access port of FIG. 7B after rotating it about its longitudinal axis by ninety degrees.

FIG. 9A is a plan view of an access port according to an embodiment of the present invention.

FIG. 9B is a cross-sectional view of FIG. 9A taken along line 9A-9A.

FIG. 9C is plan view of the access port of FIG. 9A after rotating it about its longitudinal axis by ninety degrees.

FIG. 9D is a top view of the access port of FIG. 9C.

FIG. 10A is a plan view of an access port according to an embodiment of the present invention.

FIG. 10B is a cross-sectional view of FIG. 10A taken along line 10A-10A.

FIG. 10C is plan view of the access port of FIG. 10A after rotating it about its longitudinal axis by ninety degrees.

FIG. 10D is a top view of the access port of FIG. 10C.

FIG. 11A is a plan view of a disassembled access port according to another embodiment of the present invention.

FIG. 11B is a plan view of the access port of FIG. 11A after assembly.

FIG. 11C is a plan view of the access port of FIG. 11B after rotating it about its longitudinal axis by ninety degrees.

FIG. 11D is a top view of the access port of FIG. 11C.

FIG. 12E is a longitudinal section view of the access port of FIG. 12B taken along line 12A-12A.

FIG. 12F is a perspective view of the assembled access port shown in FIGS. 12B-12E.

FIG. 12G is a cross-sectional view of the access port of FIG. 12B taken along line 12B-12B.

FIG. 12H is a perspective view of an illumination strip that can be assembled into the access port of FIG. 12A-12G.

FIG. 12I is a cross-sectional view of the illumination strip of FIG. 12H taken along line 12I-12I.

FIGS. 13A-13L illustrate events that may be carried out using an access port according to an embodiment of the present invention.

FIG. 14 is a plan view of an access port according to another embodiment of the present invention.

DETAILED DESCRIPTION OF THE INVENTION

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an instrument" includes a plurality of such instruments and reference to "the implant" includes reference to one or more implants and equivalents thereof known to those skilled in the art, and so forth.

The publications discussed herein are provided solely for their disclosure prior to the filing date of the present application. The dates of publication provided may be different from the actual publication dates which may need to be independently confirmed.

Figure 1D:
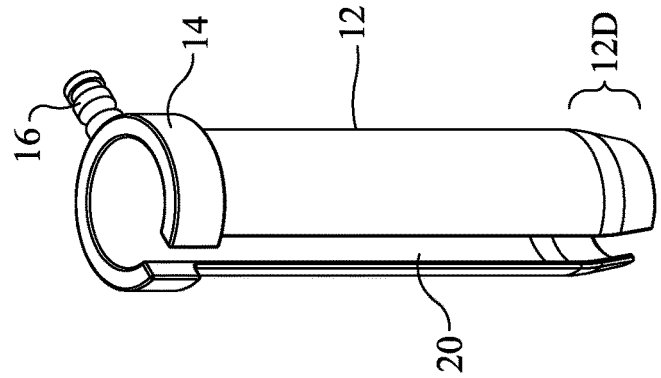
FIG. 1D is a perspective view of the access port of FIGS. 1A-1C.
Figure 1B:
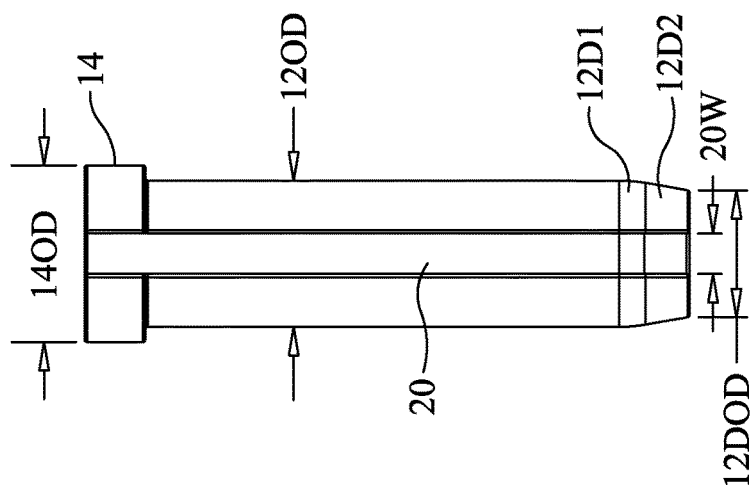
FIG. 1B is a plan view of the access port of FIG. 1A after rotating it about its longitudinal axis by ninety degrees.
Figure 1C:
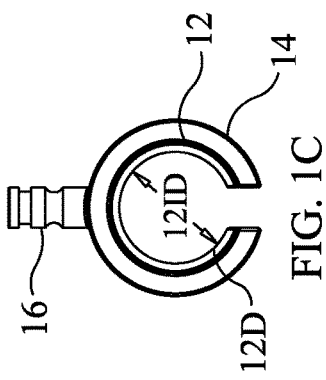
FIG. 1C is a top view of the access port of FIG. 1B.
Figure 1A:
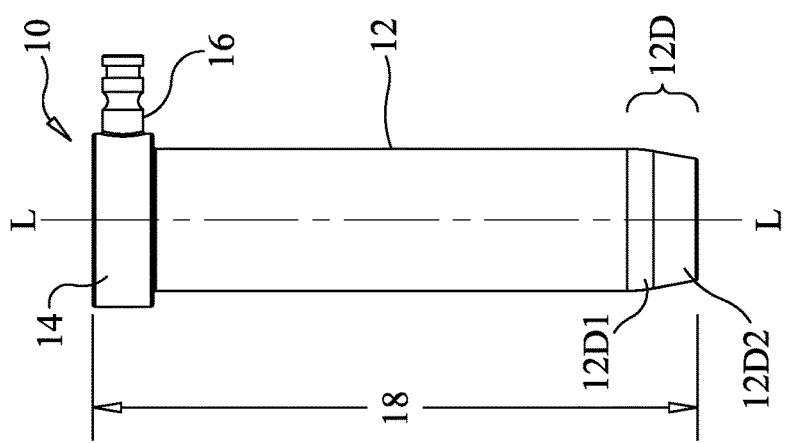
FIG. 1A is a plan view of an access port according to an embodiment of the present invention.

FIG. 1A is a plan view of an access port 10 according to an embodiment of the present invention. This and all other embodiments of access port described herein are configured and dimensioned for minimally invasive surgery, preferably, although not limited to, minimally invasive spinal surgery. Examples of preferred uses for ports 10 include posterior minimally invasive surgery to remove all or part of an intervertebral disk and perform a spinal fusion, which may include implantation of one or more implants and/or graft material into the intervertebral disk space; or lateral minimally invasive surgery to remove all or part of an intervertebral disk and perform a spinal fusion, which may include implantation of one or more implants and/or graft material into the intervertebral disk space Access port 10 includes a rigid, elongate main body portion 12 a ring portion 14 and a connector 16. In the embodiment of FIGS. 1A-1D, at least body portion 12 and ring portion 14 are integrally formed. Optionally, connector 16 may also be integrally formed with body portion 12 and ring portion 14. At least body portion 12 and ring portion 14 may be machined from a monoblock of material. The components of access port 10 may be made all from the same material, or from different materials such as aluminum, stainless steel, titanium, aluminum alloys, titanium alloys or rigid polymer. The length 18 of port 10 typically is a value in the range of from about 30 mm to about 150 mm Connector 16 extends horizontally, radially outwardly from the ring portion 14 in the embodiment of FIGS. 1A-1D and is configured to connect and fix port 10 to a stationary object, such as an operating table or other stationary object, as described in further detail below. The distal end portion 13D of port 10 is tapered along one or more taper angles to reduce the outside diameter of the port and facilitate insertion of the port through the tissues and into the intervertebral disk 4. In the embodiment shown in FIG. 1A, the distal end portion 13D includes two tapered sections, with a first section 13D1 having a taper angle less than the taper angle of the second section 13D2. The inside diameter 12ID (see FIG. 1C) of the main body tube 12 may be of any size within a range of from about 8 mm to about 32 mm and is typically tapered distally along one or more taper angles.

FIG. 1B is a plan view of the access port 10 of FIG. 1A after rotating it about its longitudinal axis L-L by ninety degrees. In this view, the connector 16 faces into the drawing sheet and is therefore not visible. Slot 20 extends through the full length of main body 12 and the full length of ring 14. In the embodiment of FIG. 1B, slot 20 has a width 20W that is substantially invariant over the length of slot 20 to minimize reduction in rigidity of the main body 12 due to the formation of the slot 20, while affording a large range of angulation to tools used in conjunction with the access port 10. Additionally main body 12 can be rotated about its longitudinal axis, either before or after insertion into the body so as to locate slot 20 at any angular position about the circumference of the main body desired, prior to fixing the access port to a fixed object via connector 16. This greatly increases the area that can be reached by the working end of a tool inserted through the access port 10. The width 20W may be a value in the range of from about 8 mm to about 18 mm. The outside diameter 120D of the non-tapered portion of main body 12 may be a value in the range of from about 8.5 mm to about 34.5 mm. The outside diameter 12DOD of the distal end of end portion 12D may be a value in the range of from about 6 mm to about 32 mm. The outside diameter 140D of the ring portion 14 may be a value in the range of from about 10.5 mm to about 40 mm.

FIG. 1C is a top view of the access port 10 of FIG. 1B. FIG. 1D is a perspective view of the access port 10 according to the embodiment of FIGS. 1A-1C.

FIG. 2A is a plan view of an access port 10 according to another embodiment of the present invention. All features not specifically described hereafter are the same as those described in regard to the embodiment of FIGS. 1A-1D. In the embodiment of FIGS. 2A-2D, connector 16 extends vertically away from the proximal end of ring portion 14. Although the specific embodiments described herein describe the connector 16 as oriented either parallel or normal to the longitudinal axis L-L of the main body 12 and ring 14, it is noted that connector 16 could be provided so as to extend from ring 14 at an acute or obtuse angle to the longitudinal axis L-L. FIG. 2B is a plan view of the access port 10 of FIG. 2A after rotating it about its longitudinal L-L axis by ninety degrees. FIG. 2C is a top view of the access port 10 of FIG. 2B. FIG. 2D is a perspective view of the access port 10 of FIGS. 2A-2C.

Figure 3F:
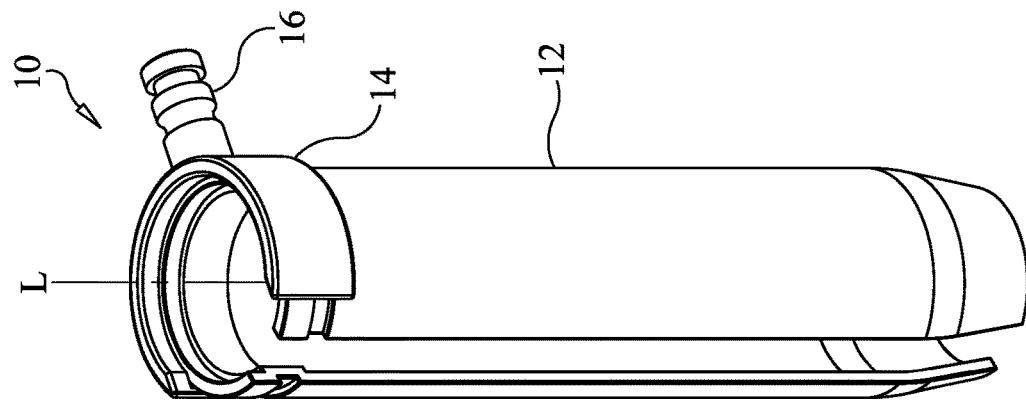
FIG. 3F is a perspective view of the assembled access port shown in FIGS. 3B-3E.
Figure 3E:
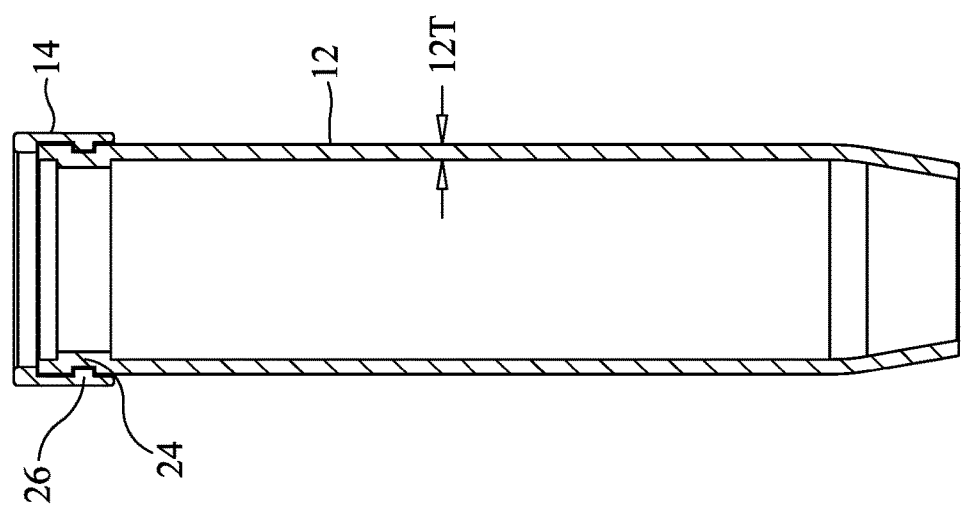
FIG. 3E is a longitudinal section view of the access port of FIG. 3B taken along line 3A-3A.

FIG. 3A is a plan view of a disassembled access port 10 according to another embodiment of the present invention. In this embodiment, ring 14 and connector 16 are constructed separately from main body 12, and are assembled to form the access port 10 shown in the assembled view of FIG. 3B. All features not specifically described hereafter are the same as those described in regard to the embodiment of FIGS. 1A-1D. In the embodiment of FIGS. 3A-3F, ring portion 14 includes a slot 22 that is wider than slot 20, which allows the main body 12 to be rotated relative to ring portion 14 over a predefined angle range even after ring portion 14 has been fixed to a stationary object, and still maintain continuity between the slots 20 and 22 so that an instrument can be slid through both slots 22 and 20. Ring portion 14 can be snap fit over the proximal end of main body 12. A groove 24 is formed in the proximal end portion of main body 12 and a ledge or shoulder or protrusion 26 is formed around the inside surface of ring portion 14. Ledge/shoulder/protrusion 26 is configured and dimensioned to mate with groove 24 when ring portion 14 is pressed down over the proximal end portion of the main body, causing the ring portion to first flex slightly outwardly and then return to the unbiased configuration shown in FIG. 3A as the protrusion 26 snap fits into groove 24 when the ring portion 14 is in the position shown in FIGS. 3B-3F, where ring portion resiliently returns into its unbiased configuration once in position to surround the proximal end portion (except for where gap 22 is located) of main body 12 as ledge 26 mates with groove 24. The thickness 12T of the main body portion tube 12 may be any value within a range of about 0.5 mm to about 2.5 mm. In the assembled configuration, main body 12 can be rotated relative to ring portion 14, about the longitudinal axis L-L. This rotational ability provides even more range of motion that instruments inserted through the access port 10 can achieve, as the location of the slot 20 can be varied by rotating the main body portion 12 relative to the ring 14, when ring 14 is fixed relative to a stationary object. In this embodiment, connector 16 extends horizontally away from the ring portion 14

Figure 3D:
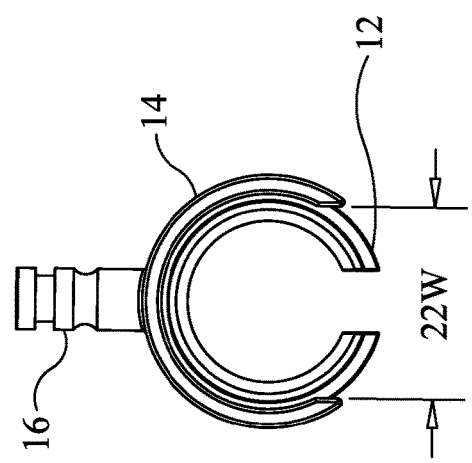
FIG. 3D is a top view of the access port of FIG. 3C.

FIG. 3C is a plan view of the access port 10 of FIG. 3B after rotating it about its longitudinal L-L axis by ninety degrees. FIG. 3D is a top view of the access port 10 of FIG. 3C. The width 22W of slot 22 may be any value with a range of from about 7 mm to about 31 mm, which provides a rotatability of the main body 12 relative to the ring portion 14 by an angle in the range of from about +45 degrees to about −45 degrees for a total range of rotatability of about 90 degrees. Of course, these angles and angle ranges could vary by design, as desired. FIG. 3F is a perspective view of the assembled access port 10 of FIGS. 3A-3E.

Figure 4C:
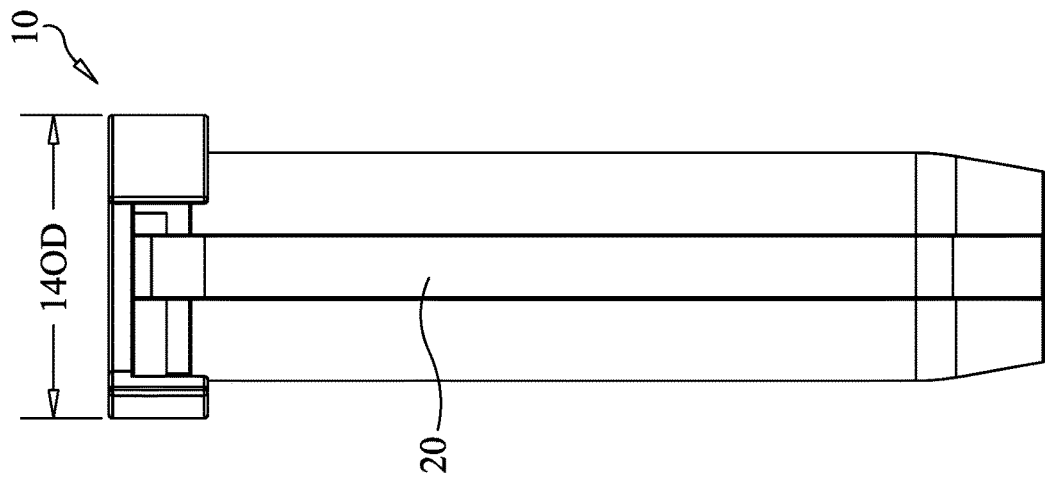
FIG. 4C is a plan view of the access port of FIG. 4B after rotating it about its longitudinal axis by ninety degrees.
Figure 4B:
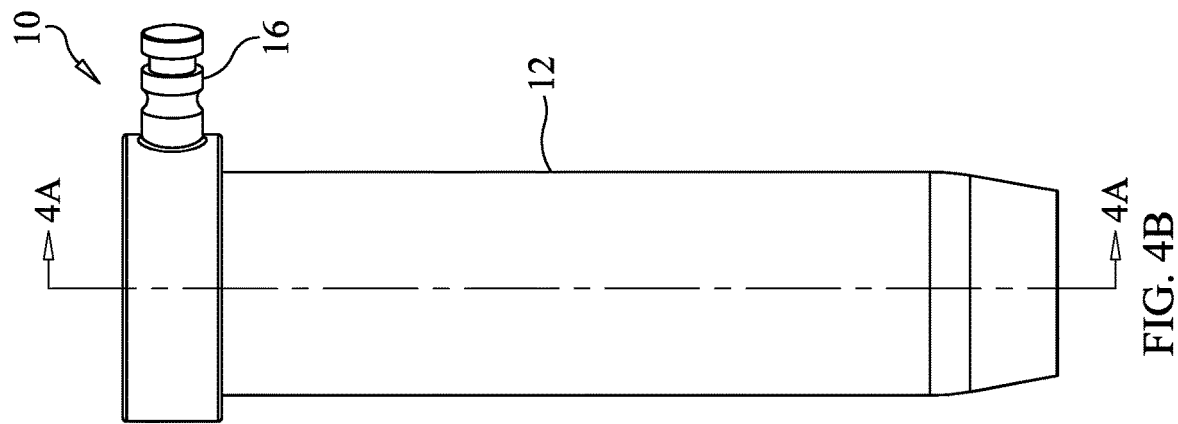
FIG. 4B is a plan view of the access port of FIG. 4A after assembly.
Figure 4A:
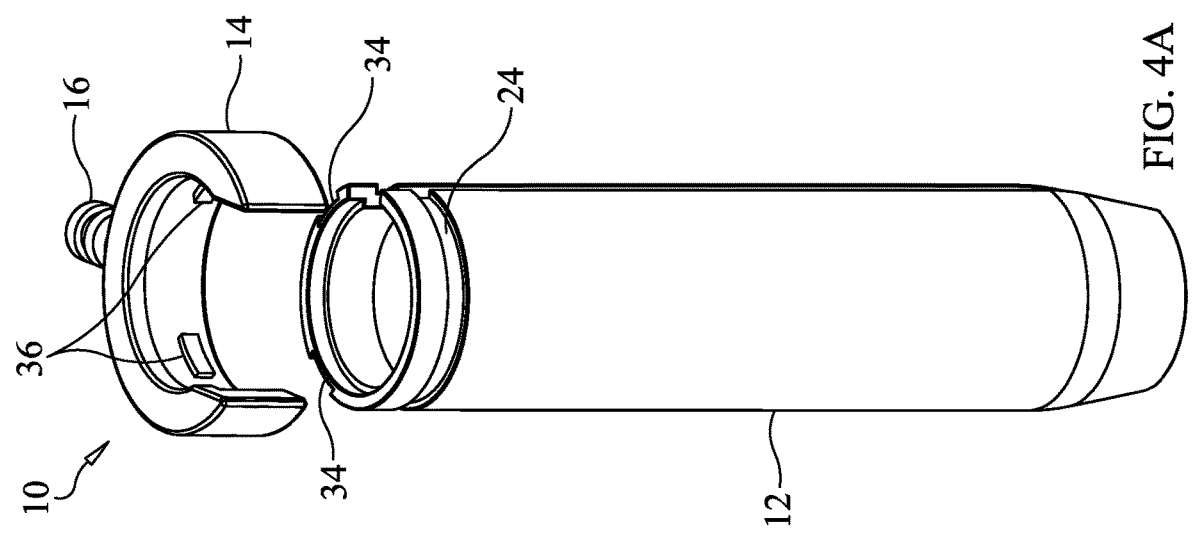
FIG. 4A is a plan view of a disassembled access port according to another embodiment of the present invention.

FIG. 4A is a plan view of a disassembled access port 10 according to another embodiment of the present invention. In this embodiment, ring portion 14 and connector 16 are constructed separately from main body 12, and are assembled to form the access port 10 shown in the assembled view of FIG. 4B. All features not specifically described hereafter are the same as those described in regard to the embodiment of FIGS. 3A-3F. In the embodiment of FIGS. 4A-4F, ring portion 14 includes a slot 22 that may be wider than slot 20. A groove 24 is formed in the proximal end portion of main body 12 and cutouts 34 are formed in the proximal end portion of the main body 12 that is proximal of the groove 24. Cutouts 34 have a depth about equal to a depth of groove 24 and open into groove 24. Tabs 36, such as rectangular or other shaped tabs are formed to extend from the inside surface of ring portion 14 and are spaced and configured so that they can pass through cutouts 34 when ring portion is fitted over the top (proximal end) of main body 12. After tabs 36 pass through cutouts 34, the ring 14 and main body 12 are rotated relative to the one another such that tabs 36 travel through groove 24 and are no longer aligned with cutouts 34. This securely attaches ring portion 14 to main body portion, so that the components cannot be separated during use, as the main body 12 cannot be rotated sufficiently during use to realign cutouts 34 with the tabs 36.

After completion of a procedure and removal of the access port from fixation to a stationary object and from a patient, the components can be reverse rotated to realign the cutouts 34 with the tabs 36 so that the ring portion 14 can be separated from the main body portion 12, if desired.

Figure 4F:
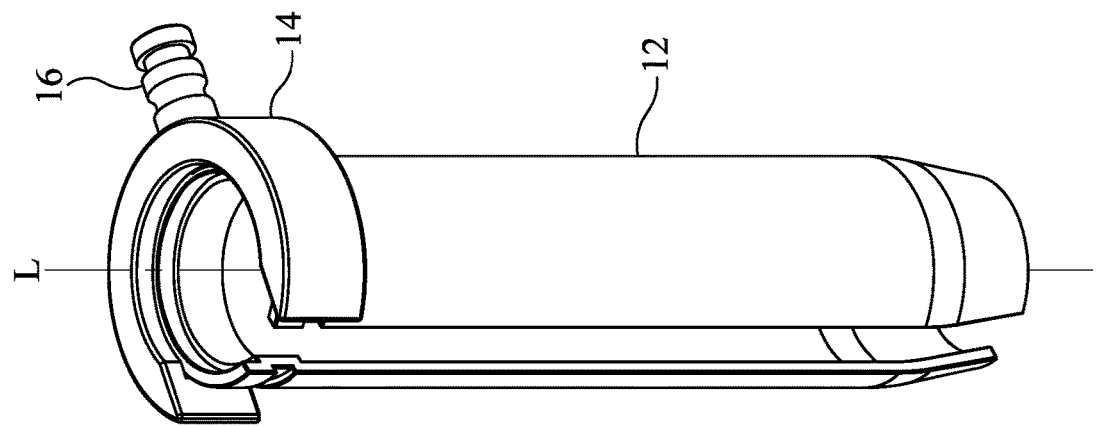
FIG. 4F is a perspective view of the assembled access port shown in FIGS. 4B-4E.
Figure 4E:
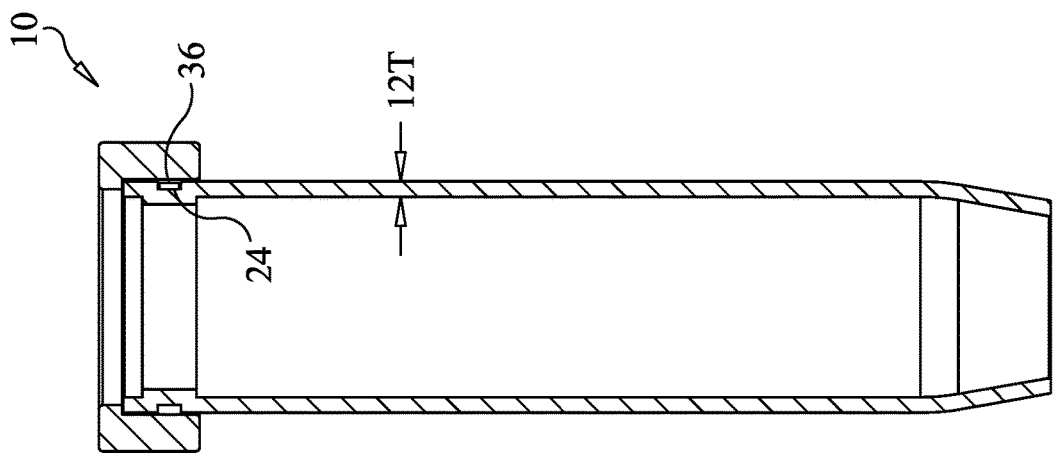
FIG. 4E is a longitudinal section view of the access port of FIG. 4B taken along line 4A-4A.
Figure 4D:
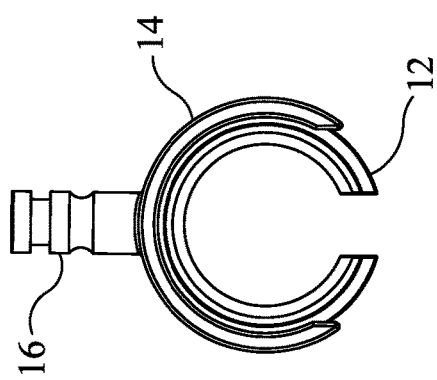
FIG. 4D is a top view of the access port of FIG. 4C.

FIG. 4C is a plan view of the access port 10 of FIG. 4B after rotating it about its longitudinal L-L axis by ninety degrees. FIG. 4D is a top view of the access port 10 of FIG. 4C. FIG. 4W is a longitudinal sectional view of the access port 10 of FIG. 4B taken along line 4A-4A. FIG. 4F is a perspective view of the assembled access port 10 of FIGS. 4A-4E.

FIG. 5A is a plan view of an access port 10 according to another embodiment of the present invention. All features not specifically described hereafter are the same as those described in regard to the embodiment of FIGS. 1A-1D. In the embodiment of FIGS. 5A-5E a pair of light ports 40 are provided through ring portion 14 to allow light cables 42 (such as fiber optic lighting, LED lighting, or the like) to be inserted therethrough and extend anywhere along the inner length of access port 10, up to, or even into the surgical site, to illuminate the workspace. However, typically the light cables are inserted through the light ports just enough so that the distal tips of the light cables 42 stay substantially flush with the inside openings of the light ports 40 and inner wall of the main body 12 to illuminate the inside of the tube/main body 12.

It is noted that the present invention is not limited to two light ports 40, as one light port 40 or more than two light ports 40 could be provided. Light ports 40 angle down toward the distal end of the access port 10 as illustrated in the longitudinal sectional view of FIG. 5B. In the embodiment of FIGS. 5A-5E, the light ports 40 are conical, with a larger inside diameter at the outer surface of the ring 14 than the inside diameter of the port 40 at the inner surface of the ring 14. For example, the inside diameter at the outer surface of the ring portion 14 may be about 5 mm when the inside diameter at the inner surface of the ring portion 14 is about 4 mm. These diameters may vary from embodiment to embodiment, and are typically in a range of about 2 mm to about 7 mm. Alternatively, ports 40 could be made cylindrical. The thickness 12T of the wall of the main body 12 in FIGS. 5A-5B is about 1.5 mm, but may be any value within a range of from about 0.5 mm to about 2.5 mm. These thickness values can also be applied to all other embodiments of the main bodies 12 of the access ports 10 described herein.

Additionally, as shown in FIG. 5C, the slot 20 tapers from a proximal end portion to a distal end portion of the access device 10, such that the proximal end portion 20P is wider than the distal end portion 20D. This provides more strength in the main body 12 at the distal end portion relative to the proximal end portion, to better resist yielding under compression forces experienced during use. It is noted that all other embodiments described herein that use a non-tapering slot 20 could alternatively be provided with a tapering slot 20 as described here. In FIG. 5C, the width 20WP of the proximal end portion of slot 20 is about 14 mm and is substantially constant over the length of the proximal end portion of slot 20, but could be any value in a range of from about 10 mm to about 18 mm, and the width 20WD of the distal end portion of slot 20 is about 12 mm and is substantially constant over the length of the distal end portion of slot 20, but could be any value in a range of from about 8 mm to about 16 mm. An intermediate portion of the slot 20 varies in width so as to join the proximal and distal end portions of the slot 20. The length of the proximal end portion of the slot 20 is greater than the length of the intermediate portion and the length of the distal end portion of the slot 20 is greater than the length of the intermediate portion. Typically the intermediate portion is provided as a transition and is less than ¼ the length of either the proximal end portion or the distal end portion of the slot 20.

FIG. 5C is a plan view of the access port of FIG. 5A after rotating it about its longitudinal axis by ninety degrees. FIG. 5D is a top view of the access port of FIG. 5C. FIG. 5E is a perspective view of the access port of FIGS. 5A-5D.

The embodiment shown in FIGS. 6A-6E is similar to the embodiment of FIGS. 5A-5E, but the connector 16 is vertically mounted, rather than horizontally mounted as in FIGS. 5A-5E. FIG. 6A is a plan view of the access port 10 according to another embodiment of the present invention. FIG. 6B is a longitudinal sectional view of the access port 10 of FIG. 6A taken along line 6A-6A. FIG. 6C is a plan view of the access port 10 of FIG. 6A after rotating it about its longitudinal axis by ninety degrees. FIG. 6D is a top view of the access port 10 of FIG. 6C. FIG. 6E is a perspective view of the access port 10 of FIGS. 6A-6D.

Figure 7F:
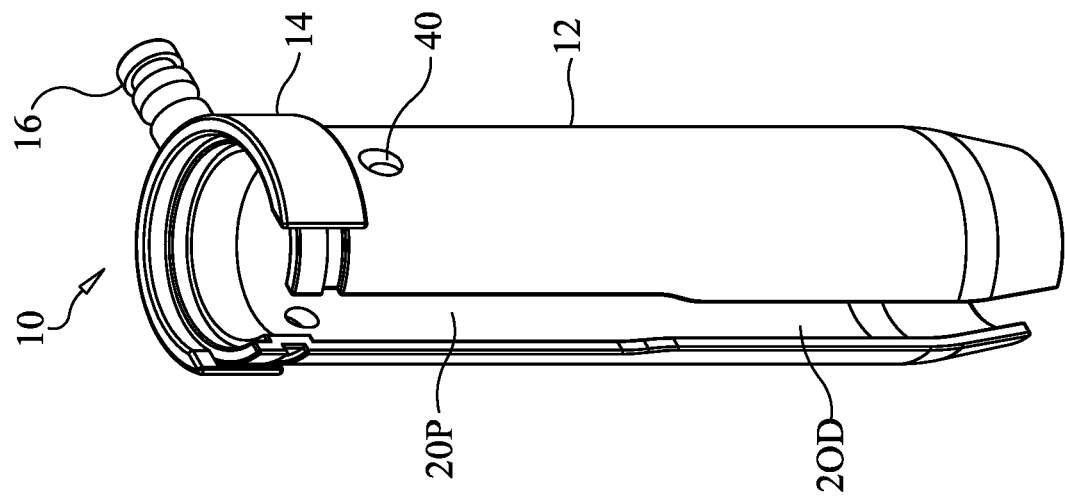
FIG. 7F is a perspective view of the assembled access port shown in FIGS. 7B-7E.
Figure 7E:
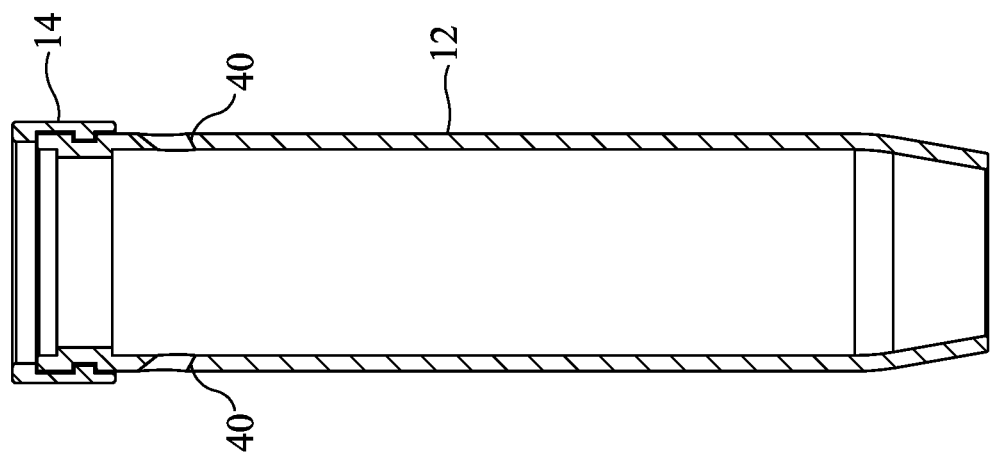
FIG. 7E is a longitudinal section view of the access port of FIG. 7B taken along line 7A-7A.
Figure 7D:
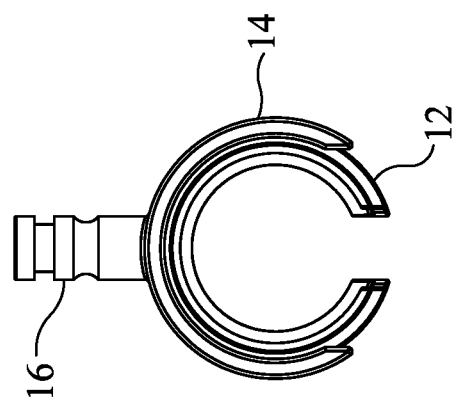
FIG. 7D is a top view of the access port of FIG. 7C.

FIGS. 7A-7F show an embodiment of the present invention that is similar to the embodiment of FIGS. 3A-3F, with differences described hereafter. FIG. 7A is a plan view of a disassembled access port 10 according to the embodiment FIGS. 7A-7F. FIG. 7A shows that light ports 40 are provided through the walls of the main body portion 12 of the access device. Light ports 40 can be the same as those described with regard to FIGS. 6A-6E, with the difference being that they are formed through the main body 12, rather than through the ring 14. As shown in FIGS. 7A and 7C, this embodiment also includes a tapered slot 20 (20P, 20D) like the embodiment of FIGS. 6A-6E. FIG. 7B is a plan view of the access port 10 of FIG. 7A after assembly. FIG. 7C is a plan view of the access port of FIG. 7B after rotating it about its longitudinal axis by ninety degrees. FIG. 7D is a top view of the access port 10 of FIG. 7C. FIG. 7E is a longitudinal section view of the access port 10 of FIG. 7B taken along line 7A-7A. FIG. 7F is a perspective view of the assembled access port 10 shown in FIGS. 7A-7E.

Figure 8C:
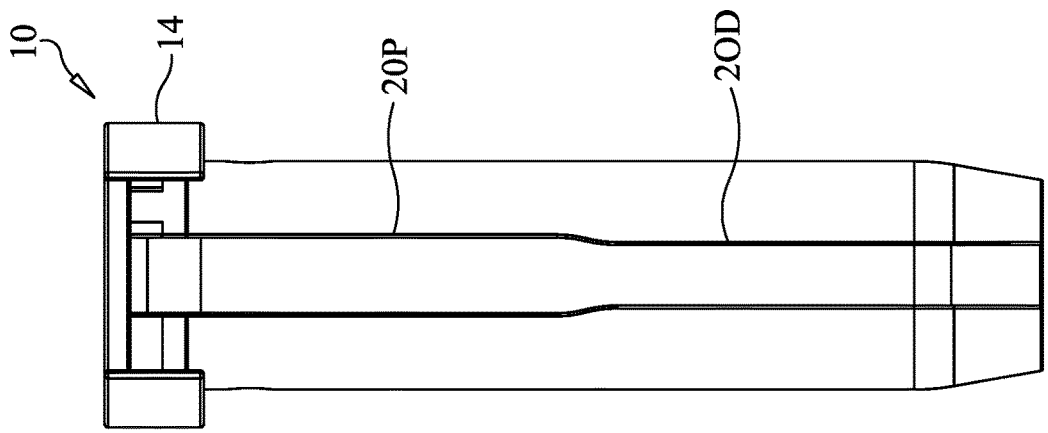
FIG. 8C is a plan view of the access port of FIG. 8B after rotating it about its longitudinal axis by ninety degrees.
Figure 8B:
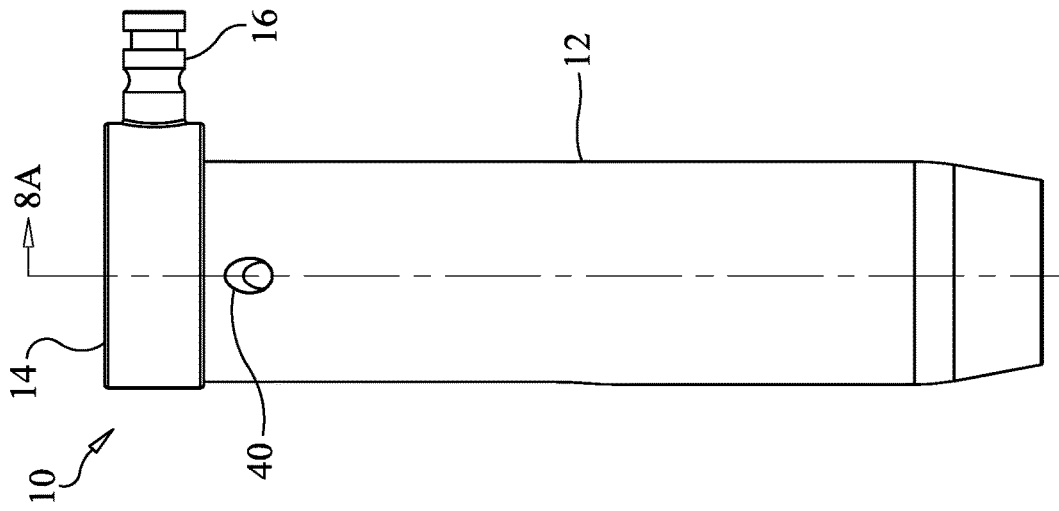
FIG. 8B is a plan view of the access port of FIG. 8A after assembly.
Figure 8A:
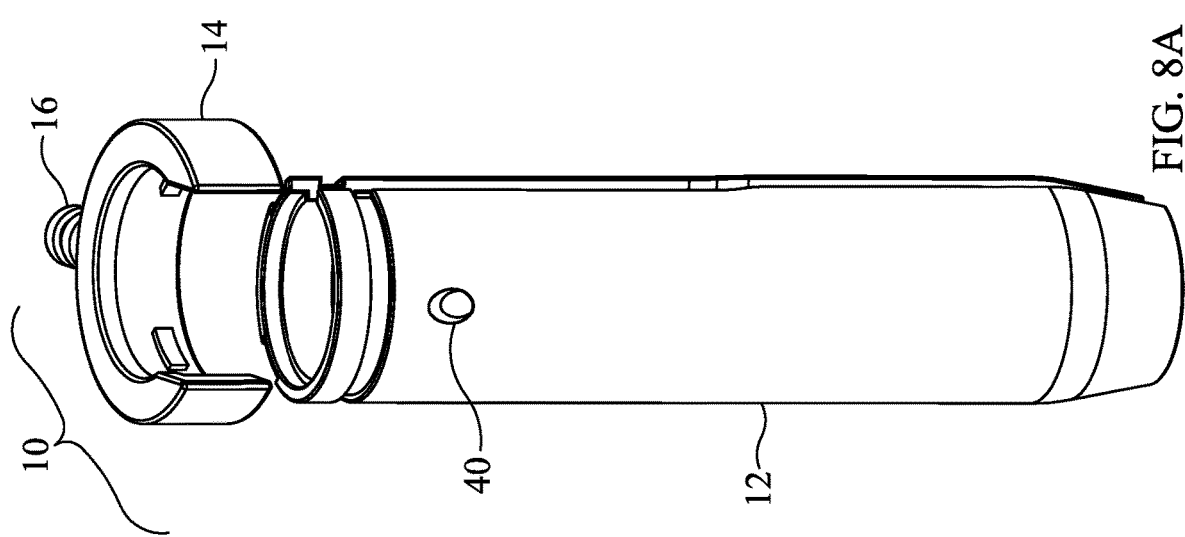
FIG. 8A is a plan view of a disassembled access port according to another embodiment of the present invention.
Figure 8F:
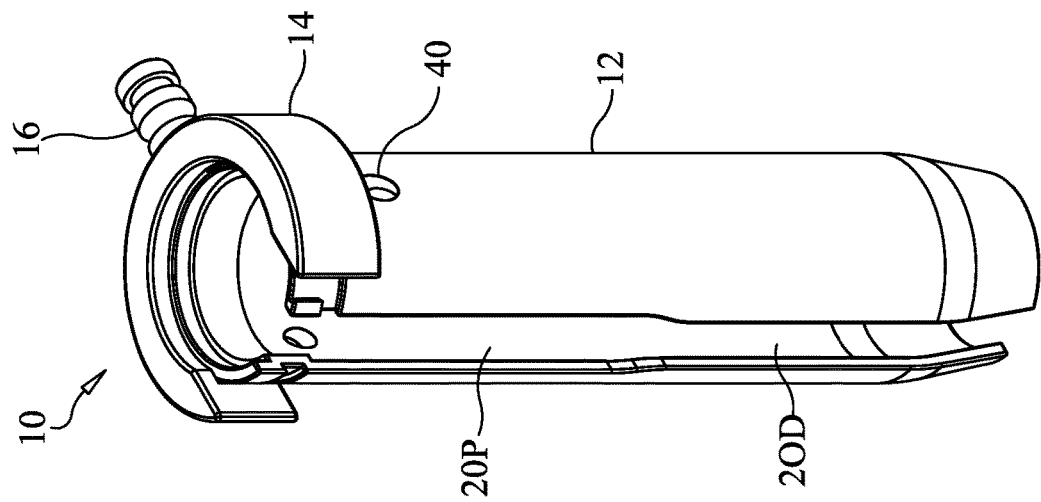
FIG. 8F is a perspective view of the assembled access port shown in FIGS. 8B-8E.
Figure 8E:
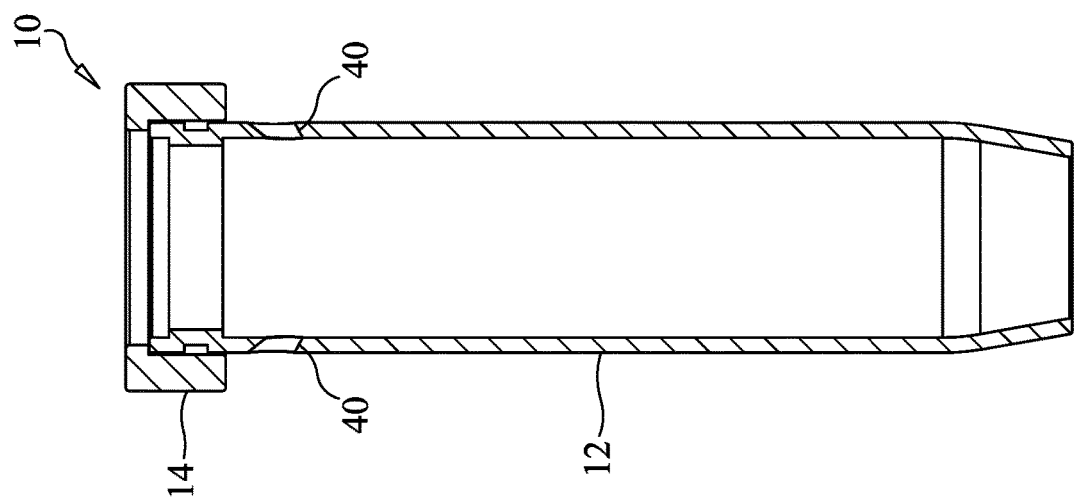
FIG. 8E is a longitudinal section view of the access port of FIG. 8B taken along line 8A-8A.
Figure 8D:
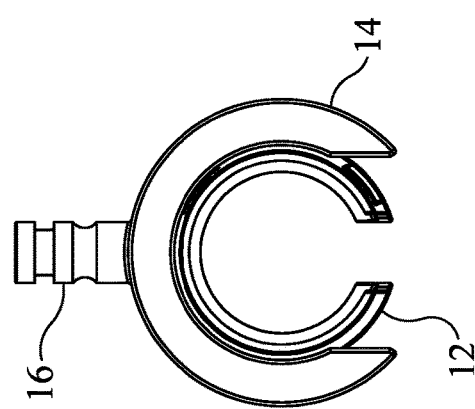
FIG. 8D is a top view of the access port of FIG. 8C.

FIGS. 8A-8F show an embodiment of the present invention that is similar to the embodiment of FIGS. 4A-4F, with differences described hereafter. FIG. 8A is a plan view of a disassembled access port 10 according to the embodiment FIGS. 8A-8F. FIG. 8A shows that light ports 40 are provided through the walls of the main body portion 12 of the access device. Light ports 40 can be the same as those described with regard to FIGS. 6A-6E, with the difference being that they are formed through the main body 12, rather than through the ring 14. As shown in FIGS. 8A and 8C, this embodiment also includes a tapered slot 20 (20P, 20D) like the embodiment of FIGS. 6A-6E. FIG. 8B is a plan view of the access port 10 of FIG. 8A after assembly. FIG. 8C is a plan view of the access port of FIG. 8B after rotating it about its longitudinal axis by ninety degrees. FIG. 8D is a top view of the access port 10 of FIG. 8C. FIG. 8E is a longitudinal section view of the access port 10 of FIG. 8B taken along line 8A-8A. FIG. 8F is a perspective view of the assembled access port 10 shown in FIGS. 8BA-8E.

Figure 9G:
FIG. 9G is a cross-sectional view of the illumination strip of FIG. 9F taken along line 9G-9G.
Figure 9F:
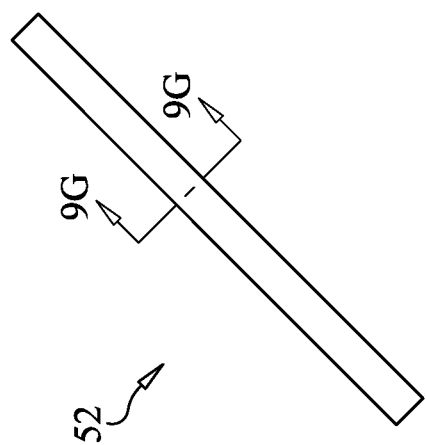
FIG. 9F is a perspective view of an illumination strip that can be assembled into the access port of FIGS. 9A-9E.
Figure 9E:
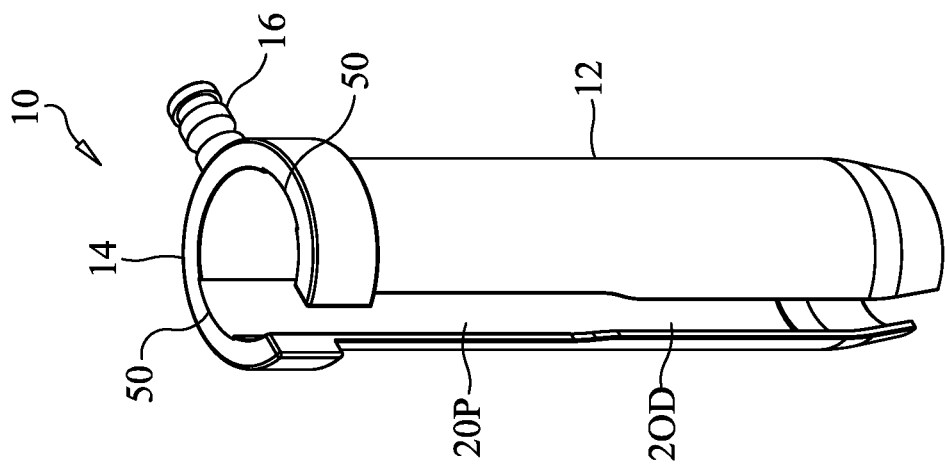
FIG. 9E is a perspective view of the access port of FIGS. 9A-9D.

FIGS. 9A-9E show a unibody or integral access port 10 according to another embodiment of the present invention, that is similar to the embodiment of FIGS. 1A-1D, with differences being described hereafter. FIG. 9A is a plan view of the access port 10 of the embodiment of FIGS. 9A-9E. FIG. 9B is a cross-sectional view of FIG. 9A taken along line 9A-9A. The cross-sectional view shows that dovetail cutouts 50 are provided in the inner wall of the main body 12. Cutouts 50 may extend the entire length of the main body 12, or only a portion thereof. Preferably, the cutouts 50 extend over substantially the full length of the main body 12. Illumination strips 52 (see FIGS. 9F-9G) can be provided as configured and shaped to slide into and mate with the dovetail cutouts 50, to provide illumination within the access port and into the surgical target area during use of the access port 10. Advantageously, the illumination strips are sized and shaped to as to be flush with the inner wall of the main body, so as not to provide any obstruction to the annulus 12A of the main body. The cross-sectional view of illumination strip 50 in FIG. 9G shows the curved, mating dovetail shape of the illumination strip 52 in cross section. In the view of FIG. 9F, it can be seen that the illumination strip is typically an elongate, rectangular shape in the plan view. Illumination strips 52 may be commercially available illumination strips such as LightMat Ultra-Thin strips, Model No. UA2550, available from Lumitex in Maryland. The ring portion 14 may also include the cutouts 50 as shown in FIG. 9E, so that the illumination strips 52 can be readily inserted into or removed from the cutouts 50. FIG. 9C is plan view of the access port 10 of FIG. 9A after rotating it about its longitudinal axis by ninety degrees. FIG. 9D is a top view of the access port 10 of FIG. 9C. FIG. 9E is a perspective view of the access port 10 of FIGS. 9A-9D. As shown in FIGS. 9C and 9E, this embodiment also includes a tapered slot 20 (20P, 20D) like the embodiment of FIGS. 6A-6E. It is further noted here, that all embodiments shown using a tapered slot 20D, 20P could alternatively be provided with a non-tapered slot like that shown and described with regard to FIG. 1B.

Figure 10G:
FIG. 10G is a cross-sectional view of the illumination strip of FIG. 10F taken along line 10G-10G.
Figure 10F:
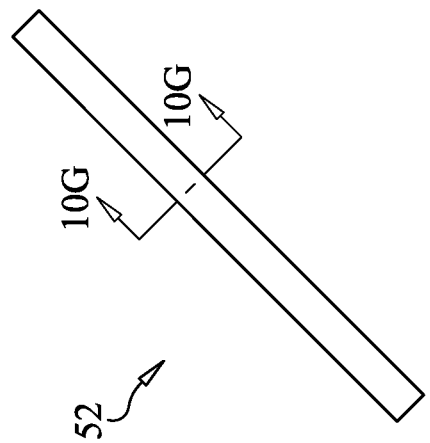
FIG. 10F is a perspective view of an illumination strip that can be assembled into the access port of FIGS. 10A-10E.
Figure 10E:
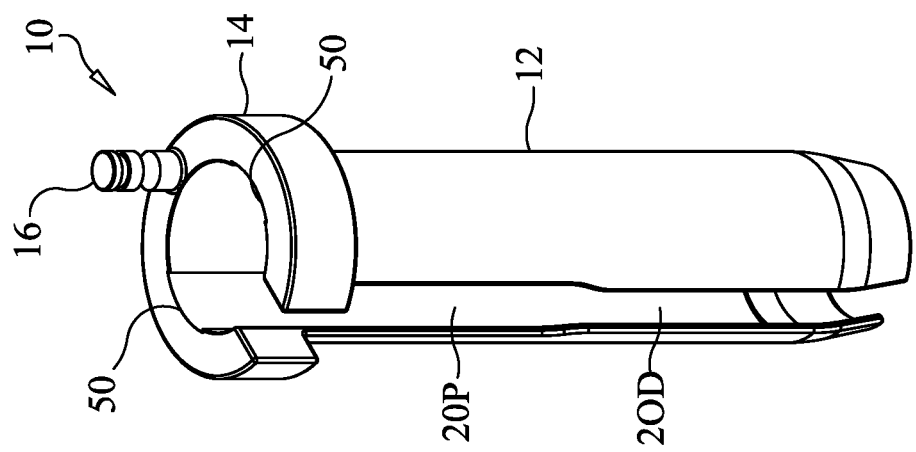
FIG. 10E is a perspective view of the access port of FIGS. 10A-10D.

FIGS. 10A-10E show a unibody or integral access port 10 according to another embodiment of the present invention, that is similar to the embodiment of FIGS. 2A-2D, with differences being described hereafter. FIG. 10A is a plan view of the access port 10 of the embodiment of FIGS. 10A-10E. FIG. 10B is a cross-sectional view of FIG. 10A taken along line 10A-10A. The cross-sectional view shows that dovetail cutouts 50 are provided in the inner wall of the main body 12. Cutouts 50 may extend the entire length of the main body 12, or only a portion thereof. Preferably, the cutouts 50 extend over substantially the full length of the main body 12. Illumination strips 52 (see FIGS. 10F-10G) can be provided as configured and shaped to slide into and mate with the dovetail cutouts 50, to provide illumination within the access port and into the surgical target area during use of the access port 10. Advantageously, the illumination strips can be sized and shaped so as to be flush with the inner wall of the main body 12, so as not to provide any obstruction to the annulus 12A of the main body 12. The cross-sectional view of illumination strip 50 in FIG. 10G shows the curved (convex surface interfaces surface of cutout 50 and concave surface faces annulus 12A), mating dovetail shape of the illumination strip 52 in cross section. In the view of FIG. 10F, it can be seen that the illumination strip is typically an elongate, rectangular shape in the plan view. The ring portion 14 may also include the cutouts 50 as shown in FIG. 10E, so that the illumination strips 52 can be readily inserted into or removed from the cutouts 50. FIG. 10C is plan view of the access port 10 of FIG. 10A after rotating it about its longitudinal axis by ninety degrees. FIG. 10D is a top view of the access port 10 of FIG. 10C. FIG. 10E is a perspective view of the access port 10 of FIGS. 10A-10D. As shown in FIGS. 10C and 10E, this embodiment also includes a tapered slot 20 (20P, 20D) like the embodiment of FIGS. 6A-6E.

Figure 11G:
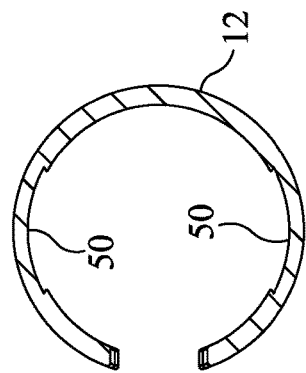
FIG. 11G is a cross-sectional view of the access port of FIG. 11B taken along line 11B-11B.
Figure 11F:
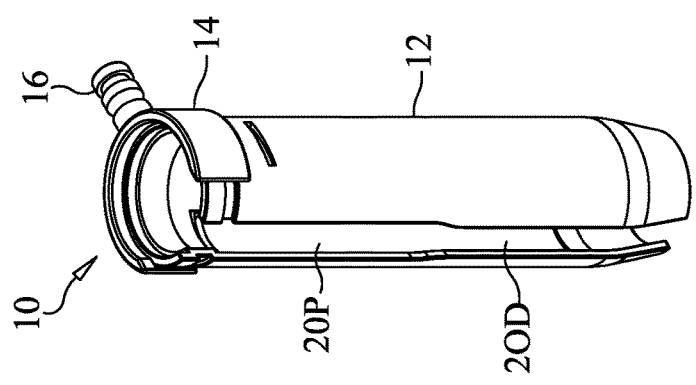
FIG. 11F is a perspective view of the assembled access port shown in FIGS. 11B-11E.
Figure 11I:
FIG. 11I is a cross-sectional view of the illumination strip of FIG. 11H taken along line 11I-11I.
Figure 11H:
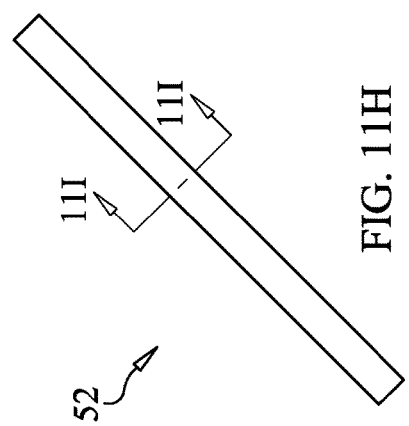
FIG. 11H is a perspective view of an illumination strip that can be assembled into the access port of FIG. 11A-11G.
Figure 11E:
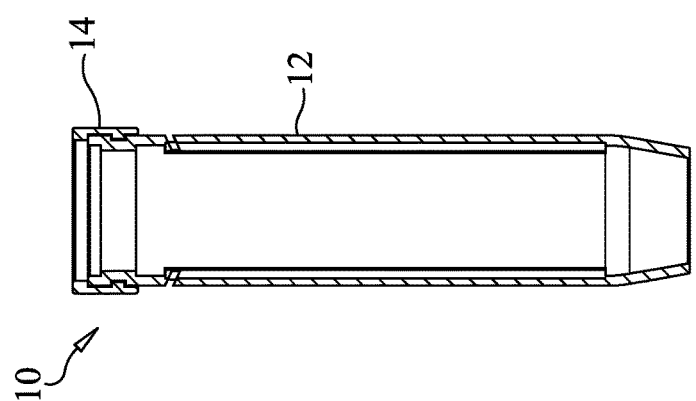
FIG. 11E is a longitudinal section view of the access port of FIG. 11B taken along line 11A-11A.

FIGS. 11A-11G show an access port 10 according to another embodiment of the present invention that is similar to the embodiment of FIGS. 7A-7F, with differences being described hereafter. FIG. 11A is a perspective, unassembled view of the access port 10. FIG. 11B is an assembled, plan view of the access port 10 of FIG. 11A. FIG. 11C is a plan view of the access port 10 of FIG. 11B after rotating it about its longitudinal axis by ninety degrees. FIG. 11D is a top view of the access port 10 of FIG. 11C. FIG. 11E is a longitudinal sectional view taken along line 11A-11A of FIG. 11B. FIG. 11F is a perspective view of the assembled embodiment of FIGS. 11B-11E. FIG. 11G is a cross-sectional view of FIG. 11B taken along line 11B-11B. The cross-sectional view shows that dovetail cutouts 50 are provided in the inner wall of the main body 12. Cutouts 50 may extend the entire length of the main body 12, or only a portion thereof. FIG. 11A shows cutouts that extend proximally only to the proximal portion that bounds groove 24 and distally only to a location proximally adjacent to the tapering distal end portion of the main body 12. Angular flat slots 54 cut through the main body 12 on either side of the main body 12 allow easy introduction of the illumination strips 52 into the mating cutouts 50. Alternatively, the cutouts 50 can extend all the way to the proximal end of main body 12, to allow the illumination strips 52 to be easily slid into the mating cutouts 50, prior to installing the ring portion 14. The ring portion 14 preferably does not include cutouts 50 (but alternatively could include cutouts 50), so that once the ring 14 is installed, this prevents illumination strips 52 from sliding back out of the cutouts 50. As shown in FIG. 11B, slots 54 may be curved to conform to the cross-sectional curvature of illumination strips 52. Slots 54 can be angled relative to the longitudinal axis L-L of the main body 12 to facilitate the insertion and placement of the illumination strips, e.g., see FIG. 11C. In the embodiment of FIG. 11C, angle 56 is about 50 degrees, although various other angles may be employed, typically with a range of from about 30 degrees to about 70 degrees. Illumination strips 52 (see FIGS. 11H-11I) can be provided as configured and shaped to slide into and mate with the dovetail cutouts 50, to provide illumination within the access port and into the surgical target area during use of the access port 10. Advantageously, the illumination strips can be sized and shaped to as to be flush with the inner wall of the main body, so as not to provide any obstruction to the annulus 12A of the main body. The cross-sectional view of illumination strip 52 in FIG. 11I shows the curved, mating dovetail shape of the illumination strip 52 in cross section. In the view of FIG. 11H, it can be seen that the illumination strip 52 is typically an elongate, rectangular shape in the plan view, although its shape may vary. The slot 20 is also provided in this embodiment as a tapered slot having proximal 20P and distal 20D slot portions, like the embodiment of FIGS. 6A-6E. Alternatively, the slot 20 could be provided as a non-tapered slot.

Figure 12C:
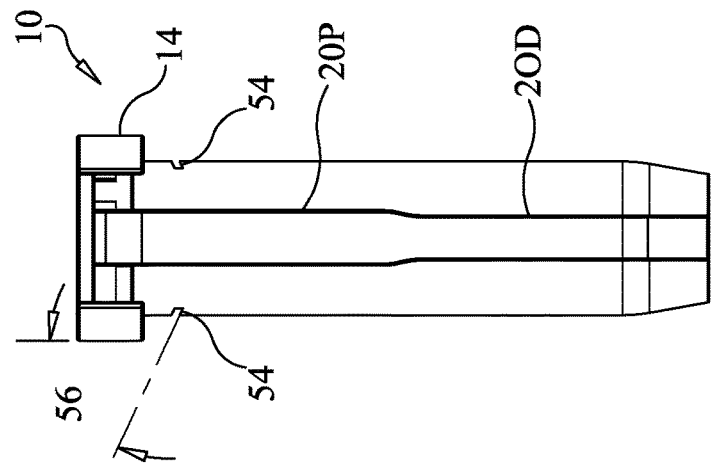
FIG. 12C is a plan view of the access port of FIG. 12B after rotating it about its longitudinal axis by ninety degrees.
Figure 12B:
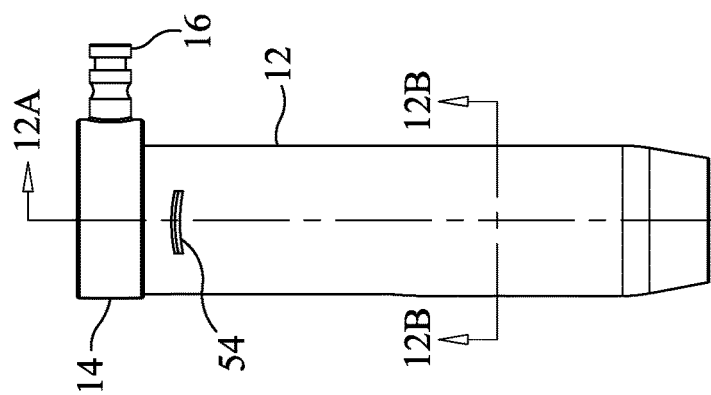
FIG. 12B is a plan view of the access port of FIG. 12A after assembly.
Figure 12D:
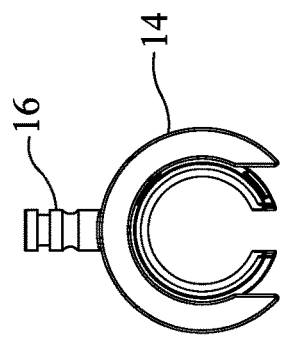
FIG. 12D is a top view of the access port of FIG. 12C.
Figure 12A:
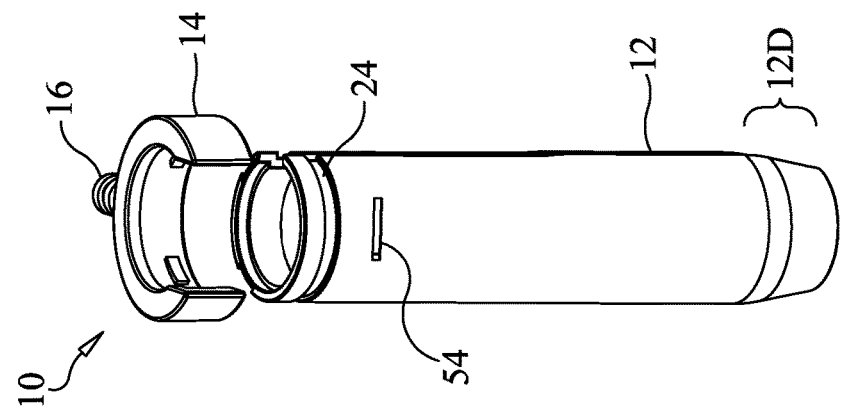
FIG. 12A is a plan view of a disassembled access port according to another embodiment of the present invention.
Figure 13A:
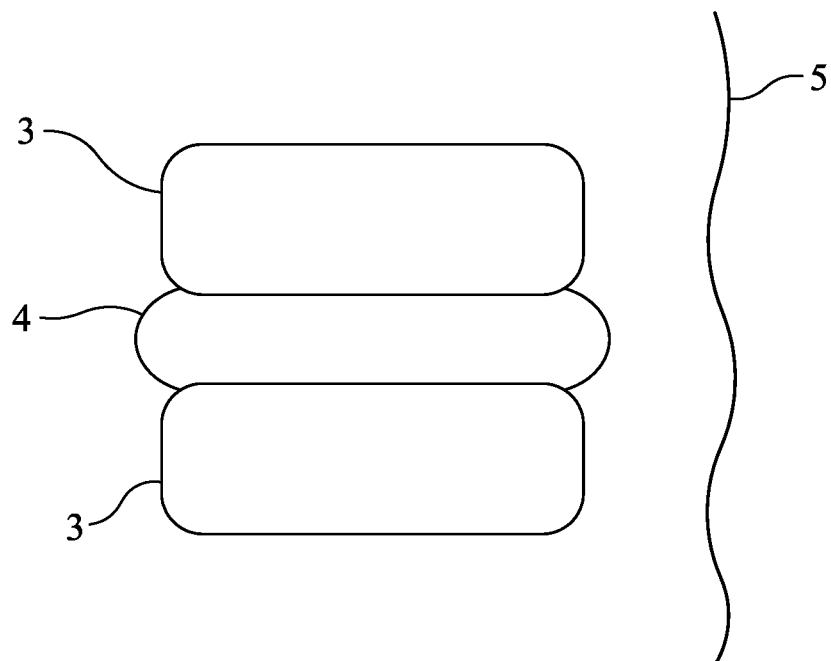
Figure 13B:
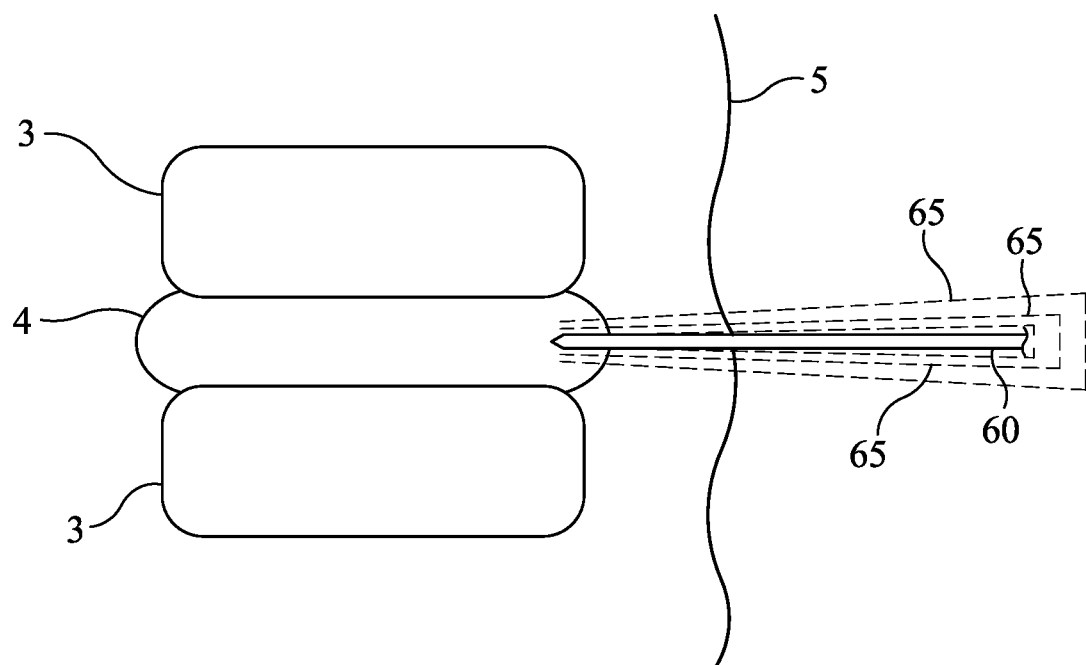

FIGS. 12A-12G show an access port 10 according to another embodiment of the present invention that is similar to the embodiment of FIGS. 8A-8F, with differences being described hereafter. FIG. 12A is a perspective, unassembled view of the access port 10. FIG. 12B is an assembled, plan view of the access port 10 of FIG. 12A. FIG. 12C is a plan view of the access port 10 of FIG. 12B after rotating it about its longitudinal axis by ninety degrees. FIG. 12D is a top view of the access port 10 of FIG. 12C. FIG. 12E is a longitudinal sectional view taken along line 12A-12A of FIG. 12B. FIG. 12F is a perspective view of the assembled embodiment of FIGS. 12B-12E. FIG. 12G is a cross-sectional view of FIG. 12B taken along line 12B-12B. The cross-sectional view shows that dovetail cutouts 50 are provided in the inner wall of the main body 12. Cutouts 50 may extend the entire length of the main body 12, or only a portion thereof. Slots 54 are provided that are the same as those described above with regard to the embodiment of FIGS. 11A-11I. Illumination strips 52 (see FIGS. 12H-12I) can be provided as configured and shaped to slide into and mate with the dovetail cutouts 50, to provide illumination within the access port and into the surgical target area during use of the access port 10. Advantageously, the illumination strips can be sized and shaped to as to be flush with the inner wall of the main body, so as not to provide any obstruction to the annulus 12A of the main body. The cross-sectional view of illumination strip 50 in FIG. 12I shows the curved, mating dovetail shape of the illumination strip 52 in cross section. In the view of FIG. 12H, it can be seen that the illumination strip 52 is typically an elongate, rectangular shape in the plan view, although its shape may vary. The slot 20 is also provided in this embodiment as a tapered slot having proximal 20P and distal 20D slot portions, like the embodiment of FIGS. 6A-6E. Alternatively, the slot 20 could be provided as a non-tapered slot. FIGS. 13A-13L illustrate events that may be carried out using an access port 10 according to an embodiment of the present invention. FIG. 13A schematically illustrates a side view of pair of adjacent vertebrae 3, an intervertebral disk 4 between the vertebrae 3 and skin 5 of the back of a patient in which a procedure is to be carried out. Typically, an incision having a length in the range of about 15 mm to about 18 mm is made through the skin 5 and the fascia and other tissues underlying the skin are manipulated with tools to provide a minimally invasive opening to the intervertebral disk 4 (surgical target location). Optionally, a K-wire or other guide 60 can be first inserted through the opening and into the intervertebral disk 4, as illustrated in FIG. 13B, and then dilators 65 of increasing diameter can be subsequently used to increase the size of the pathway leading to the surgical target location. Alternatively, the access port 10 can be installed without the use of a K wire or guide 60, for a posterior procedure, like what is illustrated in FIGS. 13A-13L. When the access port 10 is used for a lateral procedure (i.e., access port is inserted laterally of the disk 4, rather that posteriorly), a K-wire or other guide 60 is typically used to guide insertion of the access port 10. Dilators 65 can also be used in any of these approaches.

Figure 13C:
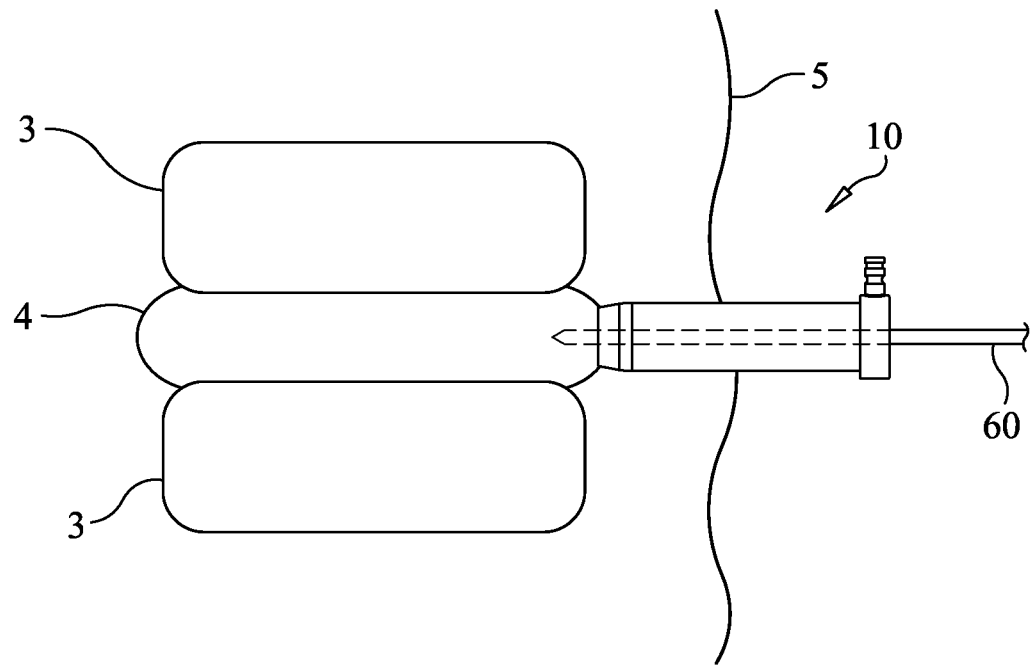
Figure 13D:
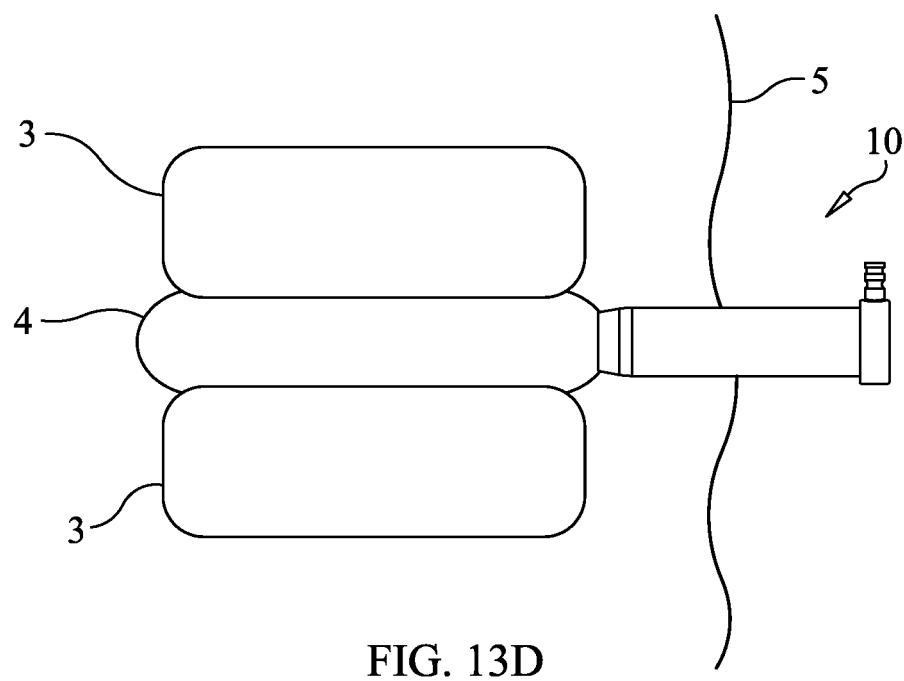

FIG. 13C illustrates the access port 10 having been inserted through the opening of the skin 5, with or without guidance by guide 60, and installed so that a distal end of the access port 10 enters or is in contact with the intervertebral disk 4. Typically, but not necessarily, it is sufficient for the distal end of the access port 10 to contact the disk 4 externally, but not enter the disk 4 space. In the optional case where a guide 60 is used, the guide is next removed from the patient and from within the access port 10, as shown in FIG. 13D. If a guide 60 was not used, the procedure appears as in FIG. 13D after insertion and placement of the access port as described with regard to FIG. 13C.

Figure 13E:
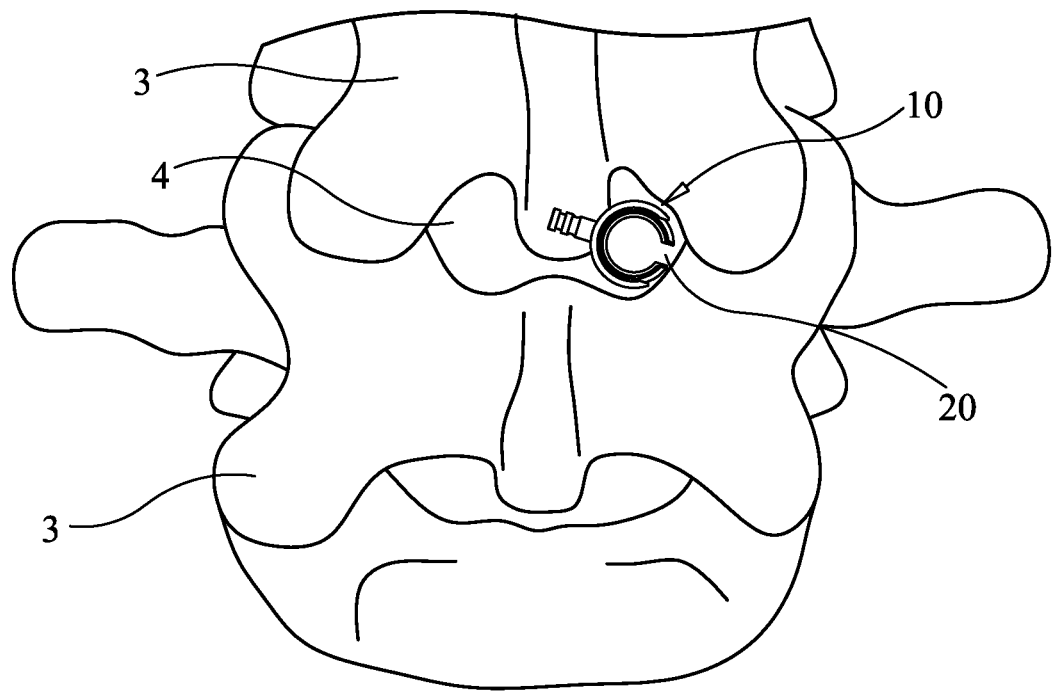
Figure 13F:
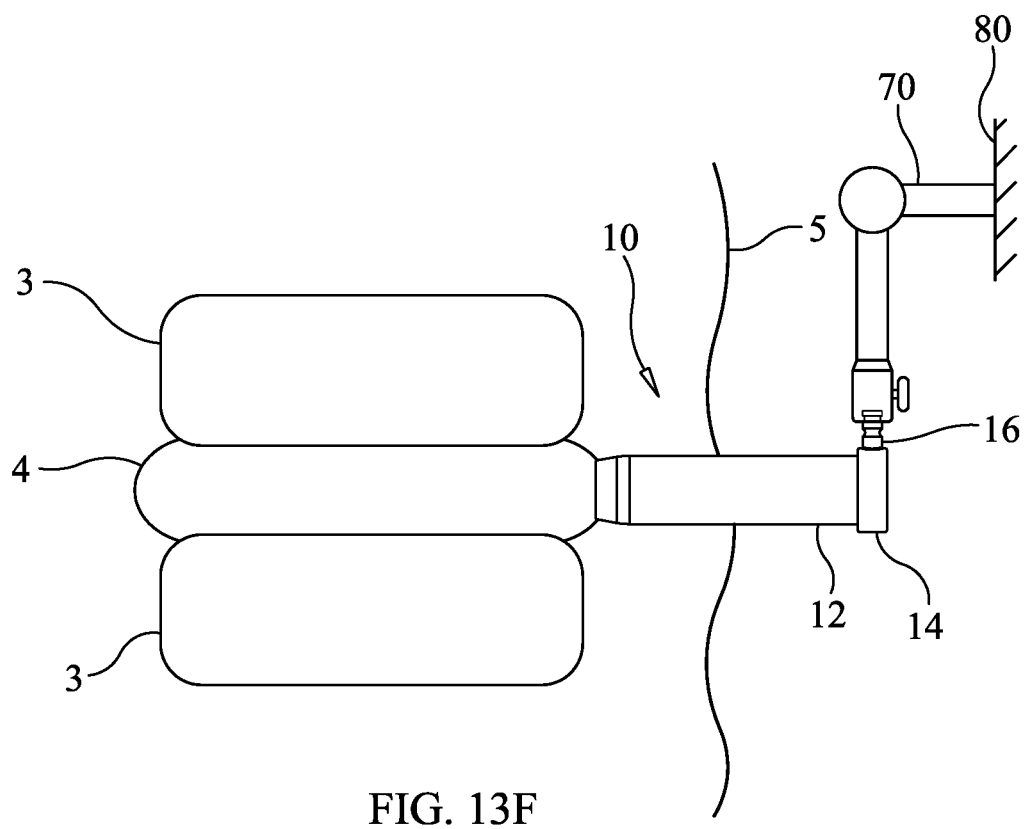

FIG. 13E is a top view of FIG. 13D. In this view, the feet of the patient are in the direction of the bottom of the drawing sheet and the surgeon would be located such that slot 20 faces toward the direction of the surgeon. The connector 16 is next connected to an interconnecting rod or linkage 70 (see FIG. 13F) that is also connected to a stationary object 80, such as the operating table or other stationary object, so that at least the ring 14 is fixed during the rest of the procedure.

Figure 13G:
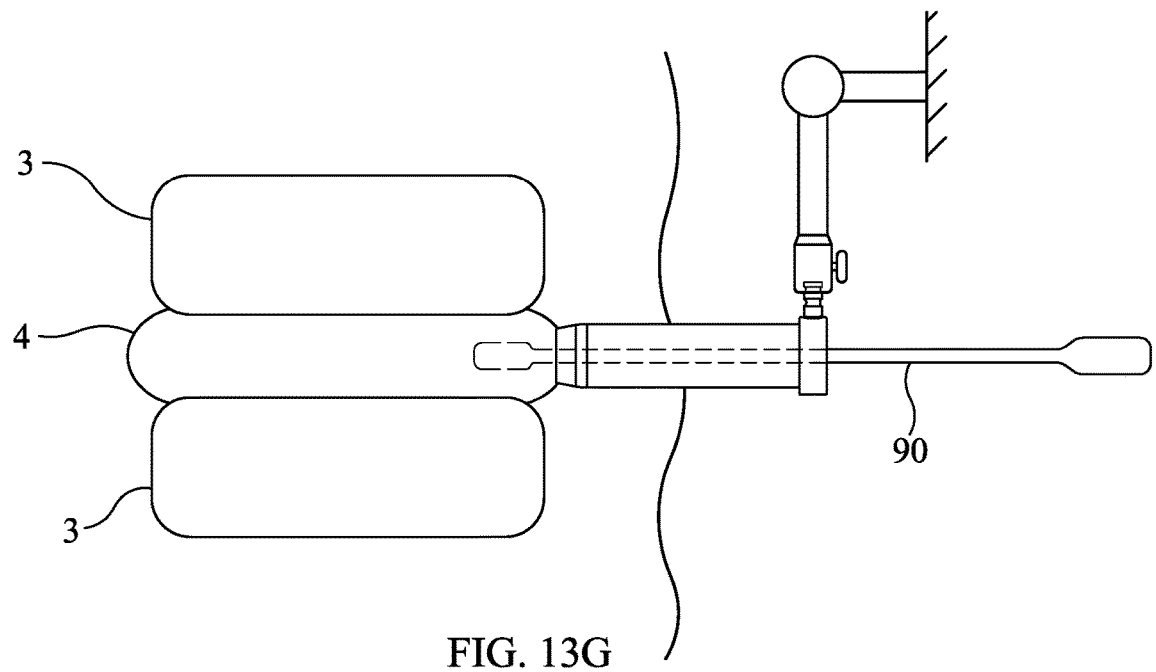
Figure 13H:
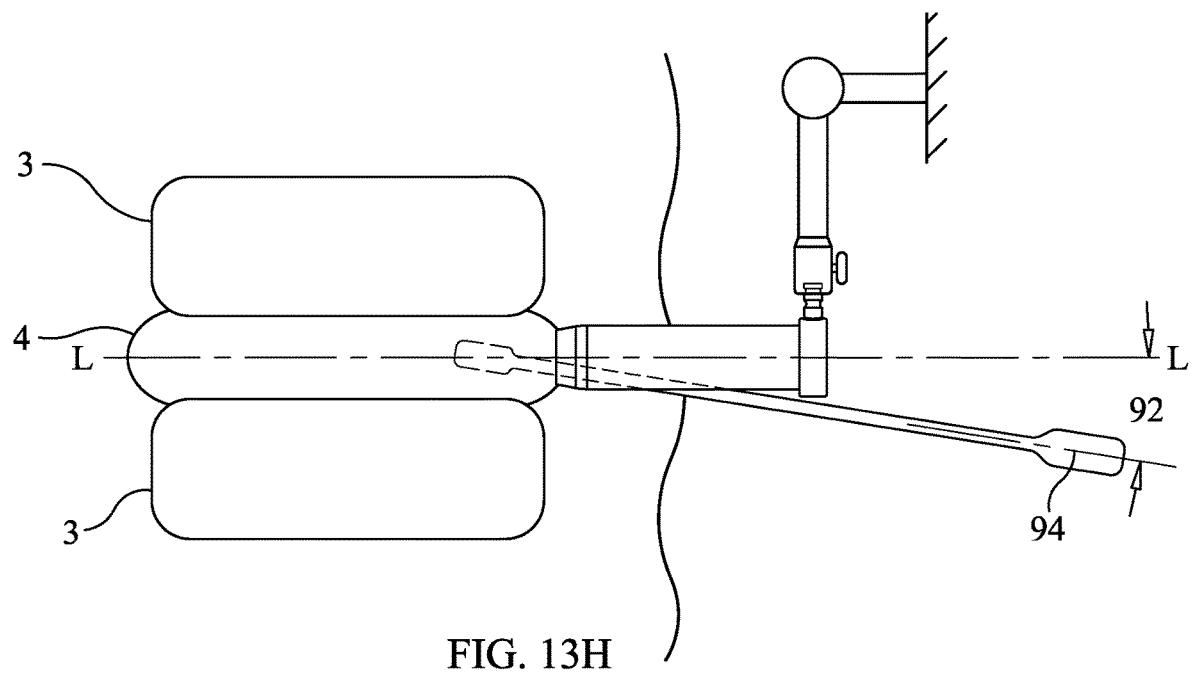

FIG. 13G illustrates an instrument 90 being inserted into the disk 4 space in a procedure to remove a herniated disk prior to implantation. Instruments 90 that may be used in this procedure include, but are not limited to: rongeurs, rasps, curettes, and cutting instruments. Suction may also be used to help remove finer particulates and liquids, such as blood, etc. In order to extend the range and angulation over which the working ends of the instruments 90 can operate, the surgeon can work the proximal end portion of the shaft of the instrument 90 through the slot 20 of the access port 10 as illustrated in FIG. 13H. Slot 20 provides the ability to angle the instrument 90 relative to the access port 10, such that the longitudinal axis 94 of the instrument shaft forms an angle 92 with the longitudinal axis L-L of the access port 10 up to 65 degrees or more, typically within a range of about 25 degrees to about 60 degrees, and in other instances, a range of from about 15 degrees to 20 degrees is sufficient. In embodiments where the main body 12 is rotatable relative to the ring portion 14, the main body can be rotated about the longitudinal axis L-L over a range of about −45 degrees to about +45 degrees, thereby further extending the range of the space that the working ends of the instruments 90 can reach.

Figure 13I:
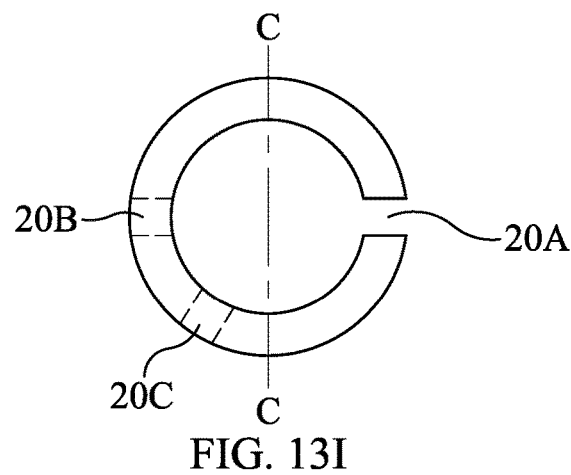
Figure 13J:
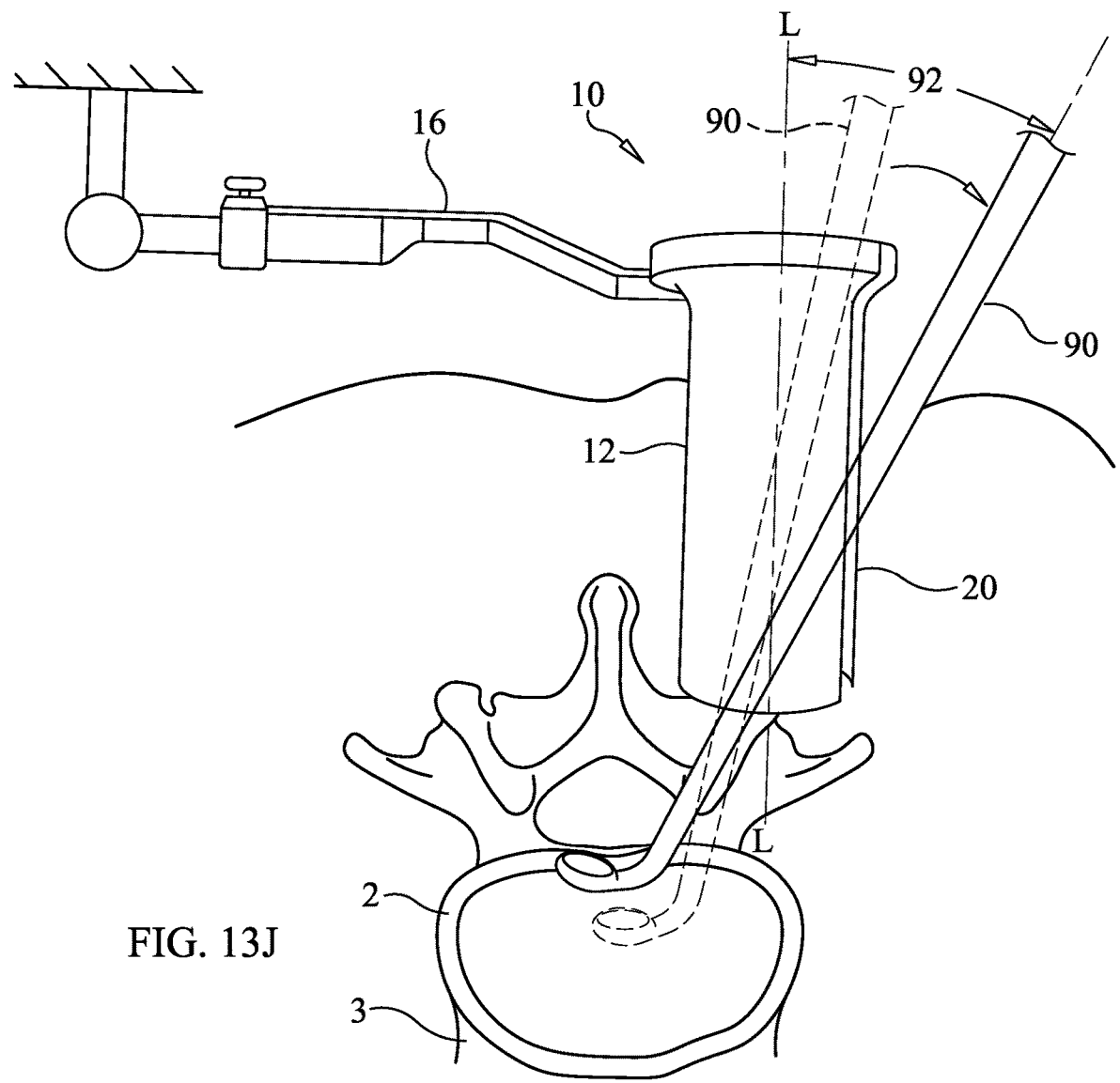

Further, as noted above, when not fixed to a stationary object, the entire access port 10 can be rotated about its longitudinal axis to further extend the range of the space that the working ends of instruments 90 can reach. FIG. 13I is a cross sectional view of the access port 10 having been rotated about its longitudinal axis by ninety degrees relative to that shown in FIG. 13H. FIG. 13J illustrates the large angulation 92 that the instrument 90 is capable of achieving relative to the longitudinal axis L-L of the access port because of the continuous slot 20 that extends so as not to limit the angulation of the tool 90. The angulation 92 is limited only by the physical structures of the body that is being operated on. The ability to rotate the access port 10 about its longitudinal axis L-L as described further increases the area that the working end of the instrument 90 can reach. Slot 20 can be oriented at any angle about the circumference of the main body 12 relative to the cranial-caudal axis, and further can be repositioned to any other angle even after insertion, fixation and working with tools 90. This increases the versatility and range of access provided by the access port 10. FIG. 13I illustrates non limiting examples of orientations 20A, 20B, 20C of the slot 20 relative to the cranial-caudal axis C-C that the present invention allows. Slot 20 can be orientated at any angle relative to the cranial-caudal axis C-C either before fixation of the access port 10 to a fixed object, or, after fixing, by unfixing, rotating and re-fixing.

After the disk 4 space has been sufficiently cleared and suctioned and all instrumentation 90 has been removed from the access port 10, one or more implants 100 (typically one or two, inserted sequentially) can be inserted through access port 10 and implanted in the intervertebral disk 4 space, using an inserter instrument 110, as illustrated in FIG. 13K. Additionally, graft material 120, such as bone particles or chips, demineralized bone matrix (DBM), paste, bone morphogenetic protein (BMP) substrates or any other bone graft expanders, or other substances designed to encourage bone ingrowth into the disk 4 space to facilitate the fusion may be implanted. Further details about implants and graft material can be found in U.S. patent application Ser. No. 12/764,614, filed Apr. 21, 2010, and U.S. Pat. No. 8,906,097, issued Dec. 9, 2014, both of which are hereby incorporated herein, in their entireties, by reference thereto.

After completion of the implantation of the implant(s) 100 and, optionally, bone graft material 120, the inserter 110 is detached from the last implant 100 implanted and removed from the access port 10 and then the access port 10 is removed and the patient is closed according to standard procedures. FIG. 13L schematically illustrates the surgical target location after completion of the closure.

FIG. 14 is a plan view of an access port 10 according to another embodiment of the present invention. The embodiment shown in FIG. 14 is the same as the embodiment of FIGS. 1A-1D, except the slot 20 does not extend through the full length of the access port 10. The slot 20 extends through the ring portion 14 and through the proximal end of the main body and over a majority of the length of the main body 12, but ends proximally of the distal end of the main body 12, As shown, the distal end of the slot ends around where the tapering of the distal end portion 12D begins, but other embodiments could include shorter or longer slots 20, wherein the length of the slot is greater than the width of the slot by a factor of at least three, typically greater than three, four or even larger factors. Preferably slot 20 extends over at least a majority of the length of the main body 12 to allow maximum angulation of instruments as described, while being kept narrow in width to maximize the rigidity of the main body 12. By maintaining the full circumference of the distal end of the main body 12, this strengthens it against compressive forces, but also reduces the range of motion of the instruments as they slide through the slot 20. This closed distal end, modified slot feature could also be provided with any of the other embodiments of access port 10 described herein.

Figure 15A:
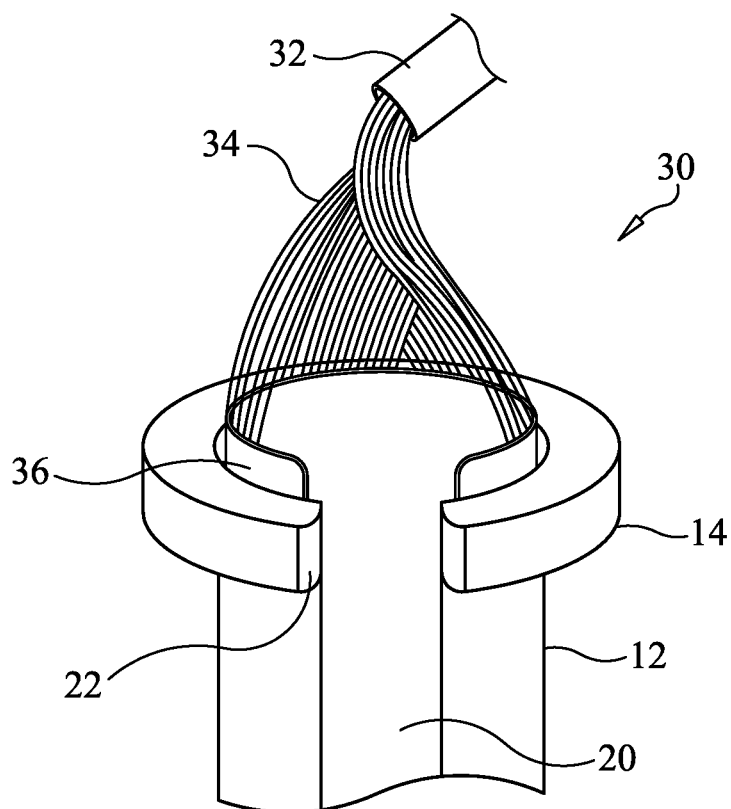
FIGS. 15A-15B are views of a light guide assembly installed in an access port according to an embodiment of the present invention.
Figure 15B:
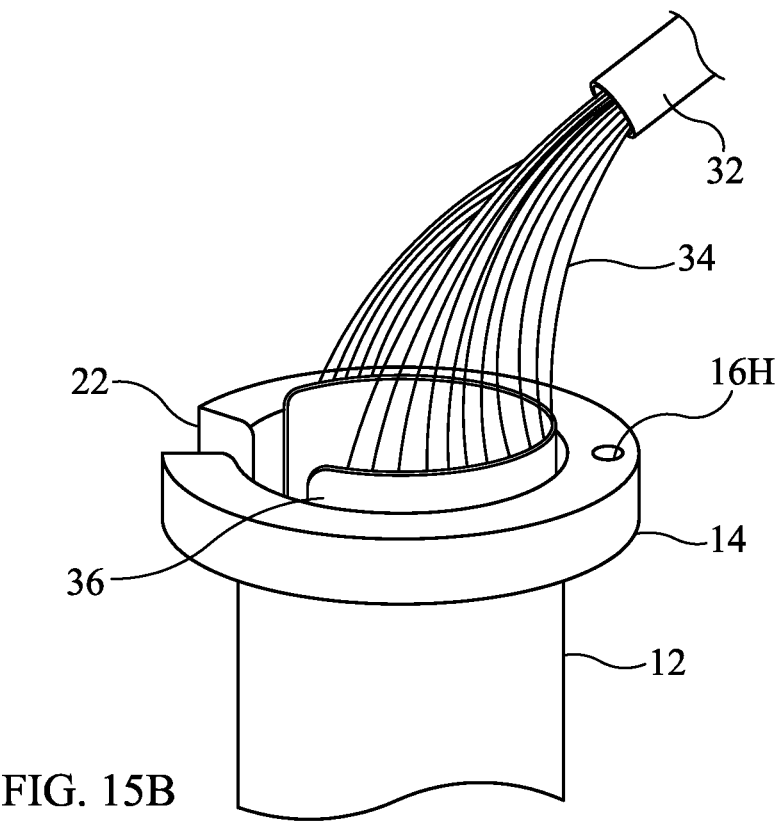

FIGS. 15A-15B illustrate an access port 10 according to another embodiment of the present invention. Although ring portion 14 is integral ring with the main body portion 12 as shown in FIGS. 15A-15B, any of the arrangements of the main body 12 and ring portion 14 (integral or separately assembled) can be used in an arrangement as described with the remaining components of FIGS. 15A-15B. Also, although a connector 16 is not shown in FIGS. 15A-15B, connector 16 could optionally be mounted, such as through hole 16H. A light guide assembly 30 is shown installed in the opening of the main body 12. Light guide assembly 30 includes a fiber optic cable 32 optical fibers/fiber optic filaments 34 and compression ring 36. Compression ring 36 is slotted, with slot 38 having a width at least equal to and typically greater than (greater than, in the embodiment shown in FIGS. 15A-15B) the width of the slot 22 in ring 14, as best shown in FIG. 15A.

Figure 15C:
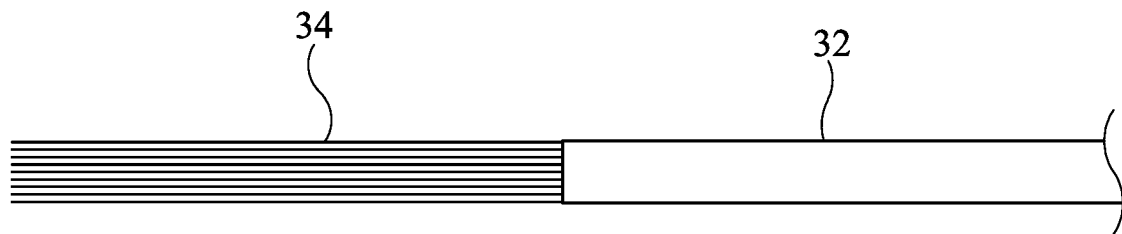
FIGS. 15C-15D illustrate steps in manufacturing a light guide assembly as shown in FIGS. 15A-15D.
Figure 15D:
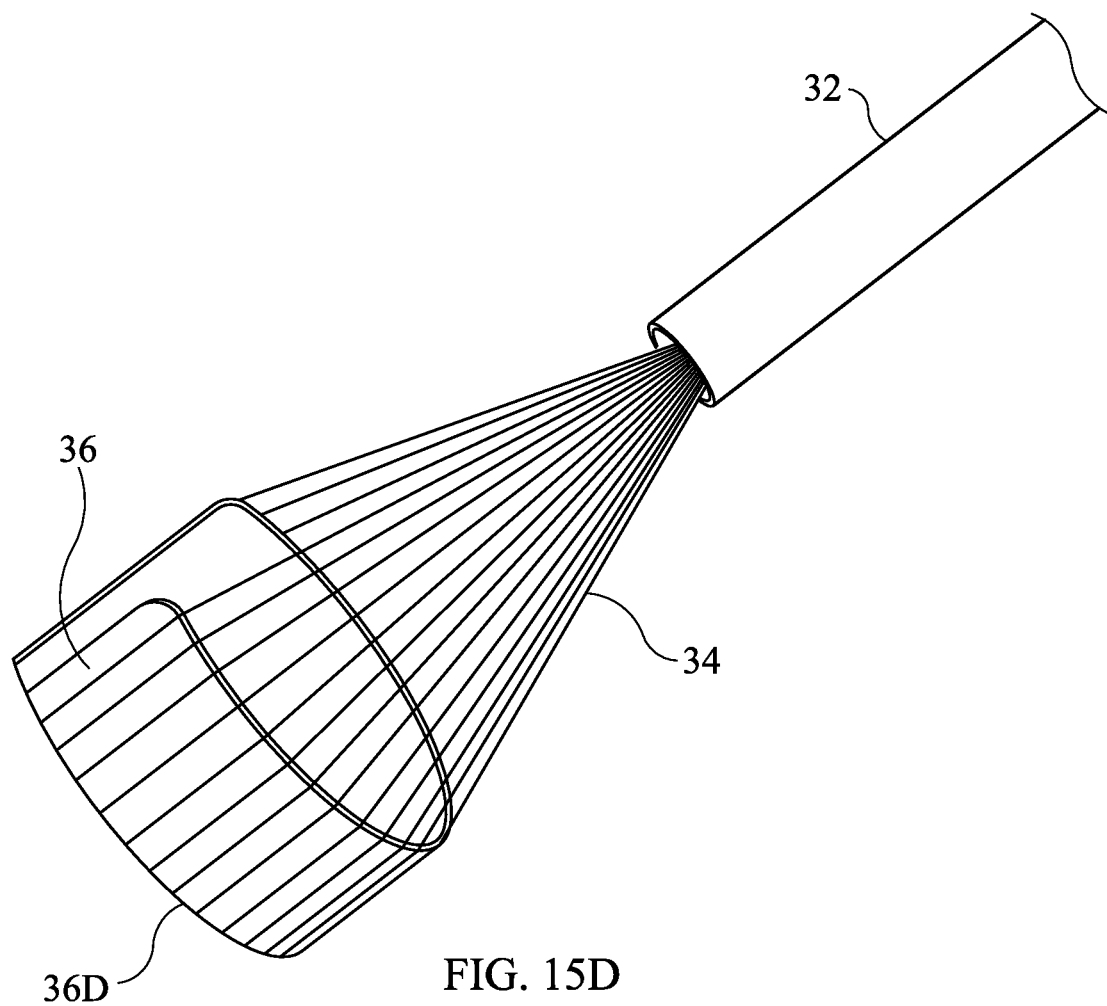

To manufacture the light guide assembly 30, the optical fibers 34 of a fiber optic cable 32 are exposed along a distal end portion of the fiber optic cable 30 as illustrated in FIG. 15C. The optical fibers 24 are next fanned out and attached around the compression ring 36 in an even distribution, as illustrated in FIG. 15D. The distal ends of the optical fibers 24 end at or just short of the distal end 36D of compression ring 36. The optical fibers 24 can be attached using adhesive, adhesive tape, or other equivalent that is sufficient to maintain adherence of the optical fibers 24 to the compression ring 36 even under sterilization environments. The optical fibers 34 of the fiber optic cable 30 are very numerous, typically in the range of about 900-1200 optical fibers, but could be more or less. This large number of optical fibers 34 when spread out form a very continuous, even light source around the inner circumference of the main body 12 as they project light along the inner walls (typically parallel to, but could be angled) of the tubular opening through the main body 12.

To install the light guide assembly to the access port, the compression ring 36 is squeezed to temporarily reduce the outside diameter thereof to allow it to be slid into the proximal end of the opening of main body 12. Thereafter, the squeezing compression force is released, allowing the compression ring to resiliently return to its unbiased, larger outside diameter. This fixes the compression ring 36 against the inner wall of the main body 12, forming a compression fit that maintains the light guide assembly 30 in the desired position relative to the main body 12 and ring 14. The optical fibers are positioned so as to direct light evenly all along the inside opening of the main body 12, thereby providing even lighting all along the length of the opening and eliminating any shadows or "dead spots" that occur with other lighting arrangements. Alternatively, the compression ring can be permanently fixed to the inner wall of the opening of the main body, such as by adhesives, welding or the like. Further alternatively, the optical fibers 24 could be adhered to the proximal end portion of the opening of the main body 12 without the compression ring 36. However, the compression fitting of the ring 36 to the inner wall of the main body provides the advantages that it can be removed, so that the access tube can be used without the light guide assembly 30 if desired and/or can be removed to simplify sterilization procedures.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An access port configured and dimensioned for use in minimally invasive surgery, said access port comprising:
    a rigid, elongate, tubular main body portion;
    a ring portion at a proximal end of said main body portion; and
    a slot extending over a length of said main body portion in a lengthwise direction;
    wherein said slot has a length and a width and extends through a wall of said main body portion, from an outside surface of said main body portion to an inside surface of said main body portion, and wherein said slot extends over a full length of said main body portion;
    wherein said width is substantially constant over at least a third of said length of said slot;
    wherein said slot extends through said wall at said proximal end of said main body portion and extends through a wall of said ring portion, so that said slot opens from inside said main body portion to outside of said ring portion, said slot being open through proximal and distal ends of said ring portion; and
    wherein said access port is open at distal and proximal ends thereof;
    wherein said slot is tapered such that said slot has a first width along a proximal portion thereof and a second width along a distal portion thereof, with an intermediate portion substantially centered along a length of said main body that tapers from said first width to said second width wherein said first width is greater than said second width, wherein said first width is constant over an entire length of said proximal portion and said second width is constant over an entire length of said second portion;
    and wherein said slot extends over a full length of said ring portion.

2. The access port of claim 1, wherein said slot allows an instrument inserted into said main body portion to be angled relative to a longitudinal axis of said main body portion by an angle greater than thirty degrees.

3. The access port of claim 1, wherein said slot extends a full length of said main body portion, from said proximal end of said main body portion to a distal end of said main body portion.

4. The access port of claim 1, further comprising a connector configured to fix at least a portion of said access port to a stationary object, wherein said connector is rigidly fixed to and extends from said ring portion.

5. The access port of claim 1, wherein said ring portion is integral with said main body portion.

6. The access port of claim 1, wherein said main body portion has a first outside diameter and said ring portion has a second outside diameter, and wherein said second outside diameter is greater than said first outside diameter.

7. The access port of claim 1, wherein said main body portion is rotatable relative to said ring portion, about a longitudinal axis of said main body portion.

8. The access port of claim 7, wherein said slot is a first slot, and wherein said ring portion comprises a second slot that aligns with said first slot when said ring portion is mounted on said main body portion.

9. The access port of claim 8, wherein said first slot has a first width and said second slot has a second width, wherein said second width is greater than said first width to allow said second slot to remain aligned with said first slot upon rotation of said main body portion relative to said ring portion.

10. The access port of claim 4, wherein said connector is substantially aligned with a longitudinal axis of said main body portion.

11. The access port of claim 4, wherein a longitudinal axis of said connector is substantially perpendicular to a longitudinal axis of said main body portion.

12. The access port of claim 1, wherein a distal end portion of said main body is tapered, so that an outside diameter of said distal end portion decreases in a direction from proximal to distal.

13. The access port of claim 1, wherein said main body portion comprises a groove extending circumferentially in an outer surface of a proximal end portion of said main body portion;
    wherein said ring portion comprises a ledge extending radially inward from an inner surface of said ring portion; and
    wherein said ledge mates with said groove upon mounting said ring portion to said main body portion.

14. The access port of claim 1, wherein said main body portion comprises a groove extending circumferentially in an outer surface of a proximal end portion of said main body portion and at least one cutout in the outer surface extending to a proximal end of said main body and communicating with said groove;
    wherein said ring portion comprises at least one tab extending radially inward from an inner surface of said ring portion, said at least one tab being configured and dimensioned to slide through said at least one cutout, respectively;

wherein, upon mounting said ring portion to said main body portion, said at least one tab passes through said at least one cutout and into said groove.

15. The access port of claim 1, further comprising at least one lighting implement extending along at least a portion of said main body portion in an annulus of said main body portion; wherein said main body portion is open at a distal end thereof.

16. The access port of claim 4, further comprising at least one light port extending from an outside surface of said access port to an inside surface of said access port; and
at least one lighting implement extending through said at least one light port and along at least a portion of said main body portion in an annulus of said main body portion.

17. The access port of claim 16, wherein said at least one light port extends through said ring portion.

18. The access port of claim 1, further comprising at least one longitudinally extending cutout in an inner wall of said main body portion; and
at least one light strip mounted in said at least one longitudinally extending cutout, respectively; wherein said main body portion is open at a distal end thereof.

19. The access port of claim 18, wherein said at least one light strip is flush with said inner wall of said main body portion.

20. The access port of claim 18, further comprising at least one slot extending through a wall of said main body portion and communicating with said at least one cutout, respectively, wherein said at least one slot is configured and dimensioned to allow said at least one light strip to be inserted therethrough and installed in said at least one cutout, respectively.

21. The access port of claim 1, in combination with an instrument configured to extend through said access port, wherein said instrument includes a distal end portion and an elongate shaft extending proximally of said distal end portion, wherein said distal end portion is configured to be inserted through an open proximal end of said access port and advanced to extend distally of a distal end of said access port and wherein said shaft can be rotated about a transverse axis thereof to pass into said slot and to extend through said slot, to provide increased range of motion of said distal end portion of said instrument.

22. The access port of claim 1, wherein said access port is configured and dimensioned for use in minimally invasive spine surgery.

23. The access port of claim 1, further comprising a light guide assembly installed in a proximal end portion of said tubular main body portion,
wherein said light guide assembly comprises a fiber optic cable having optical fibers, said optical fibers being fanned out over an inner circumference of said proximal end portion to provide even lighting throughout a tubular opening of said tubular main body portion and a surgical target targeted by a distal end opening of said tubular opening.

24. The access port of claim 23, wherein said light guide assembly further comprises a split compression ring, said optical fibers being adhered to said split compression ring and terminating at or proximal of a distal end of said split compression ring.

25. A method of performing minimally invasive surgery, said method comprising:
inserting an access port through the skin of a patient and positioning the access port adjacent or into a surgical target location, wherein the access port includes a rigid, elongate, tubular main body portion; a ring portion at a proximal end of said main body portion; and a slot extending over a length of said main body portion in a lengthwise direction; wherein said slot has a length and a width and extends through a wall of said main body portion, from an outside surface of said main body portion to an inside surface of said main body portion, and wherein said slot extends over a full length of said main body portion; wherein said width is substantially constant over at least a third of said length of said slot; wherein said slot extends through said wall at said proximal end of said main body portion and extends through a wall of said ring portion, so that said slot opens from inside said main body portion to outside of said ring portion, said slot being open through proximal and distal ends of said ring portion; and wherein said access port is open at distal and proximal ends thereof; wherein said slot is tapered such that said slot has a first width along a proximal portion thereof and a second width along a distal portion thereof, with an intermediate portion substantially centered along a length of said main body that tapers from said first width to said second width wherein said first width is greater than said second width, wherein said first width is constant over an entire length of said proximal portion and said second width is constant over an entire length of said second portion; and wherein said slot extends over a full length of said ring portion;
inserting an instrument through the access port such that a distal end portion of the instrument extends into the surgical target location; and
manipulating the instrument to pass a shaft portion of the instrument through at least a portion of the slot, wherein said instrument is manipulatable so as to angle said shaft relative to a longitudinal axis of said access port from a minimal angle of zero degrees to a maximum angle greater than thirty degrees and to any angle therebetween.

26. The method of claim 25, further comprising fixing at least a portion of the access port to a stationary object.

27. The method of claim 26, wherein the access port includes a ring portion at a proximal end portion thereof, the ring portion including a connector extending therefrom, wherein the ring portion is fixed to the stationary object by the connector.

28. The method of claim 27, wherein the main body portion is rotatable relative to the ring portion, said method further comprising rotating the main body portion relative to the ring portion to further increase the range of motion of the instrument.

29. The method of claim 25 wherein the surgical target location is in the spine of the patient.

30. The method of claim 29, wherein the surgical target location is an intervertebral disk space.

31. An access port configured and dimensioned for use in minimally invasive surgery in combination with an instrument configured to extend through said access port;
said access port comprising:
a rigid, elongate, tubular main body portion;
a ring portion at a proximal end of said main body portion; and
a slot extending over a length of said main body portion in a lengthwise direction;
wherein said slot has a length and a width and extends through a wall of said main body portion, from an outside surface of said main body portion to an inside surface of said main body portion, and wherein said slot extends over a full length of said main body portion;

wherein said width is substantially constant over at least a third of said length of said slot;

wherein said slot extends through said wall at said proximal end of said main body portion and extends through a wall of said ring portion, so that said slot opens from inside said main body portion to outside of said ring portion, said slot being open through proximal and distal ends of said ring portion; and wherein said access port is open at distal and proximal ends thereof; and wherein said instrument includes a distal end portion and an elongate shaft extending proximally of said distal end portion, wherein said distal end portion-is configured to be inserted through an open proximal end of said access port and advanced to extend distally of a distal end of said access port and wherein said shaft can be rotated about a transverse axis thereof to pass into said slot and to extend through said slot, to provide increased range of motion of said distal end portion of said instrument.

32. An access port configured and dimensioned for use in minimally invasive surgery, said access port comprising:
 a rigid, elongate, tubular main body portion;
 a ring portion at a proximal end of said main body portion; and
 a slot extending over a length of said main body portion in a lengthwise direction;

wherein said slot has a length and a width and extends through a wall of said main body portion, from an outside surface of said main body portion to an inside surface of said main body portion, and wherein said slot extends over a full length of said main body portion;

wherein said width is substantially constant over at least a third of said length of said slot;

wherein said slot extends through said wall at said proximal end of said main body portion and extends through a wall of said ring portion, so that said slot opens from inside said main body portion to outside of said ring portion, said slot being open through proximal and distal ends of said ring portion; and wherein said access port is open at distal and proximal ends thereof;

said access port further comprising a light guide assembly installed in a proximal end portion of said tubular main body portion;

wherein said light guide assembly comprises a fiber optic cable having optical fibers, said optical fibers being fanned out over an inner circumference of said proximal end portion to provide even lighting throughout a tubular opening of said tubular main body portion and a surgical target targeted by a distal end opening of said tubular opening; and wherein said light guide assembly further comprises a split compression ring, said optical fibers being adhered to said split compression ring and terminating at or proximal of a distal end of said split compression ring.

* * * * *